(12) United States Patent
Walsh

(10) Patent No.: US 7,990,549 B2
(45) Date of Patent: Aug. 2, 2011

(54) METHOD AND APPARATUS FOR OPTICALLY MEASURING PERIODIC STRUCTURES USING ORTHOGONAL AZIMUTHAL SAMPLE ORIENTATION

(75) Inventor: Phillip Walsh, Austin, TX (US)

(73) Assignee: Jordan Valley Semiconductors Ltd., Migdal Ha'emek (IL)

( * ) Notice: Subject to any disclaimer, the term of this patent is extended or adjusted under 35 U.S.C. 154(b) by 0 days.

(21) Appl. No.: 12/592,773

(22) Filed: Dec. 2, 2009

(65) Prior Publication Data

US 2010/0177324 A1 Jul. 15, 2010

Related U.S. Application Data

(63) Continuation of application No. 11/998,263, filed on Nov. 29, 2007, now abandoned.

(60) Provisional application No. 60/872,010, filed on Nov. 30, 2006.

(51) Int. Cl.
*G01B 11/30* (2006.01)

(52) U.S. Cl. ........ 356/612; 356/601; 356/625; 356/138; 356/73; 702/82; 718/104

(58) Field of Classification Search ................. 356/601, 356/625, 600, 612, 138, 73; 702/82; 718/104
See application file for complete search history.

(56) References Cited

U.S. PATENT DOCUMENTS 3,091,154 A 1/1961 Hall
(Continued)

FOREIGN PATENT DOCUMENTS

CN 2430682 Y 5/2001
(Continued)

OTHER PUBLICATIONS

Lalanne, "Improved Formulation Of The Coupled-Wave Method For Two Dimensional Gratings", Optical Society Of America, vol. 14, No. 7, Jul. 1997, pp. 1592-1598.
(Continued)

*Primary Examiner* — Tarifur R. Chowdhury
*Assistant Examiner* — Isiaka O Akanbi
(74) *Attorney, Agent, or Firm* — D. Kligler I.P. Services Ltd.

(57) ABSTRACT

An optical metrology apparatus for measuring periodic structures using multiple incident azimuthal (phi) and polar (theta) incident angles is described. One embodiment provides the enhanced calculation speed for the special case of phi=90 incidence for 1-D (line and space) structures, which has the incident plane parallel to the grating lines, as opposed to the phi=0 classical mounting, which has incident plane perpendicular to the grating lines. The enhancement reduces the computation time of the phi=90 case to the same order as the corresponding phi=0 case, and in some cases the phi=90 case can be significantly faster. One advantageous configuration consists of two measurements for each sample structure, one perpendicular to the grating lines and one parallel. This provides additional information about the structure, equivalent to two simultaneous angles of incidence, without excessive increase in computation time. Alternately, in cases where the computation for phi=90 is faster than the corresponding phi=0 incidence, it may be advantageous to measure parallel to the grating lines only. In the case where two sets of incident angles are used, the incident light can be polarized to provide a total of four sets of data—$R_s^0$, $R_p^0$, $R_s^{90}$, $R_p^{90}$—for each incident polar angle, all from the same structure.

18 Claims, 5 Drawing Sheets

U.S. PATENT DOCUMENTS

| | | |
|---|---|---|
| 3,160,752 A | 12/1964 | Bennett |
| 3,572,951 A | 3/1971 | Rothwarf et al. |
| 3,751,643 A | 8/1973 | Dill et al. |
| 3,825,347 A | 7/1974 | Kaiser |
| 4,029,419 A | 6/1977 | Schumann et al. |
| 4,040,750 A | 8/1977 | Zwiener |
| 4,368,983 A | 1/1983 | Bennett |
| 4,645,349 A | 2/1987 | Tabata |
| 4,729,657 A | 3/1988 | Cooper et al. |
| 4,837,603 A * | 6/1989 | Hayashi ........................ 356/369 |
| 4,899,055 A | 2/1990 | Adams |
| 4,984,894 A | 1/1991 | Kondo |
| 5,042,949 A | 8/1991 | Greenberg et al. |
| 5,045,704 A | 9/1991 | Coates |
| 5,120,966 A | 6/1992 | Kondo |
| 5,128,549 A | 7/1992 | Kaya |
| 5,164,790 A | 11/1992 | McNeil et al. |
| 5,182,618 A | 1/1993 | Heinonen |
| 5,241,366 A | 8/1993 | Bevis et al. |
| 5,251,006 A | 10/1993 | Hongis et al. |
| 5,357,448 A | 10/1994 | Stanford |
| 5,388,909 A | 2/1995 | Johnson et al. |
| 5,432,607 A * | 7/1995 | Taubenblatt .................. 356/364 |
| 5,440,141 A | 8/1995 | Horie |
| 5,452,091 A | 9/1995 | Johnson |
| 5,486,701 A | 1/1996 | Norton et al. |
| 5,493,401 A | 2/1996 | Horie et al. |
| 5,581,350 A | 12/1996 | Chen et al. |
| 5,607,800 A | 3/1997 | Ziger |
| 5,608,526 A | 3/1997 | Piwonka-Corle et al. |
| 5,686,993 A | 11/1997 | Kokubo et al. |
| 5,703,692 A | 12/1997 | McNeil et al. |
| 5,739,909 A | 4/1998 | Blayo et al. |
| 5,747,813 A | 5/1998 | Norton et al. |
| 5,754,296 A | 5/1998 | Law |
| 5,771,094 A | 6/1998 | Carter |
| 5,777,733 A | 7/1998 | Radziuk |
| 5,781,304 A | 7/1998 | Kotidis et al. |
| 5,784,167 A | 7/1998 | Ho |
| 5,798,837 A | 8/1998 | Aspnes et al. |
| 5,805,285 A | 9/1998 | Johs et al. |
| 5,867,276 A | 2/1999 | McNeil et al. |
| 5,880,831 A | 3/1999 | Buermann et al. |
| 5,900,939 A | 5/1999 | Aspnes et al. |
| 5,903,351 A | 5/1999 | Jeong et al. |
| 5,917,594 A | 6/1999 | Norton |
| 5,963,329 A | 10/1999 | Conrad et al. |
| 5,991,022 A | 11/1999 | Buermann et al. |
| 6,052,401 A | 4/2000 | Wieser et al. |
| 6,091,485 A | 7/2000 | Li et al. |
| 6,122,052 A | 9/2000 | Barnes et al. |
| 6,128,085 A | 10/2000 | Buermann et al. |
| 6,129,807 A | 10/2000 | Grimbergen et al. |
| 6,181,427 B1 | 1/2001 | Yarussi et al. |
| 6,184,529 B1 | 2/2001 | Contini |
| 6,184,984 B1 | 2/2001 | Lee et al. |
| 6,226,086 B1 | 5/2001 | Holbrook et al. |
| 6,261,853 B1 | 7/2001 | Howell et al. |
| 6,265,033 B1 | 7/2001 | Hilliard |
| 6,275,292 B1 | 8/2001 | Thakur et al. |
| 6,278,519 B1 | 8/2001 | Rosencwaig et al. |
| 6,281,674 B1 | 8/2001 | Huang |
| 6,297,880 B1 | 10/2001 | Rosencwaig et al. |
| 6,304,326 B1 | 10/2001 | Aspnes et al. |
| 6,313,466 B1 | 11/2001 | Olsen et al. |
| 6,327,035 B1 | 12/2001 | Li et al. |
| 6,340,602 B1 | 1/2002 | Johnson et al. |
| 6,361,646 B1 | 3/2002 | Bibby, Jr. et al. |
| 6,392,756 B1 | 5/2002 | Li et al. |
| 6,411,385 B2 | 6/2002 | Aspnes et al. |
| 6,414,302 B1 | 7/2002 | Freeouf |
| 6,417,921 B2 | 7/2002 | Rosencwaig et al. |
| 6,433,878 B1 | 8/2002 | Niu et al. |
| 6,453,006 B1 | 9/2002 | Koppel |
| 6,483,580 B1 | 11/2002 | Xu et al. |
| 6,485,872 B1 | 11/2002 | Rosenthal et al. |
| 6,525,829 B1 | 2/2003 | Powell et al. |
| 6,538,731 B2 | 3/2003 | Niu et al. |
| 6,549,279 B2 | 4/2003 | Adams et al. |
| 6,556,303 B1 | 4/2003 | Rangarajan et al. |
| 6,572,951 B2 | 6/2003 | Hasegawa et al. |
| 6,580,510 B2 | 6/2003 | Nawracala |
| 6,590,656 B2 | 7/2003 | Xu et al. |
| 6,608,690 B2 | 8/2003 | Niu et al. |
| 6,630,673 B2 | 10/2003 | Khalil et al. |
| 6,630,996 B2 | 10/2003 | Rao et al. |
| 6,633,831 B2 | 10/2003 | Nikoonahad et al. |
| 6,643,354 B2 | 11/2003 | Koppel et al. |
| 6,654,131 B2 | 11/2003 | Opsal et al. |
| 6,657,736 B1 | 12/2003 | Finarov et al. |
| 6,657,737 B2 | 12/2003 | Kimba et al. |
| 6,665,075 B2 | 12/2003 | Mittleman et al. |
| 6,673,637 B2 | 1/2004 | Wack et al. |
| 6,704,661 B1 | 3/2004 | Opsal et al. |
| 6,710,865 B2 | 3/2004 | Forouhi et al. |
| 6,713,753 B1 | 3/2004 | Rovira et al. |
| 6,713,775 B2 | 3/2004 | Chelvayohan et al. |
| 6,721,052 B2 | 4/2004 | Zhao et al. |
| 6,734,968 B1 | 5/2004 | Wang et al. |
| 6,765,676 B1 | 7/2004 | Buermann |
| 6,768,785 B2 | 7/2004 | Koppel |
| 6,768,967 B2 | 7/2004 | Johnson et al. |
| 6,775,015 B2 | 8/2004 | Bischoff et al. |
| 6,778,273 B2 | 8/2004 | Norton et al. |
| 6,778,911 B2 | 8/2004 | Opsal et al. |
| 6,801,309 B1 | 10/2004 | Nelson |
| 6,806,951 B2 | 10/2004 | Wack et al. |
| 6,806,971 B2 | 10/2004 | Finarov |
| 6,813,034 B2 | 11/2004 | Rosenewaig et al. |
| 6,819,426 B2 | 11/2004 | Sezginer et al. |
| 6,856,408 B2 | 2/2005 | Raymond |
| 6,879,395 B2 | 4/2005 | Oka et al. |
| 6,891,626 B2 | 5/2005 | Niu et al. |
| 6,897,456 B2 | 5/2005 | Hasegawa et al. |
| 6,897,807 B2 | 5/2005 | Kishigami et al. |
| 6,898,537 B1 | 5/2005 | McGahan |
| 6,909,507 B2 | 6/2005 | Norton et al. |
| 6,917,419 B2 | 7/2005 | Fielden et al. |
| 6,919,957 B2 | 7/2005 | Nikoonahad et al. |
| 6,934,025 B2 | 8/2005 | Opsal et al. |
| 6,979,578 B2 | 12/2005 | Venugopal |
| 6,982,792 B1 | 1/2006 | Woollam et al. |
| 6,987,832 B2 | 1/2006 | Koppel et al. |
| 7,006,235 B2 | 2/2006 | Levy et al. |
| 7,026,165 B2 | 4/2006 | DeGrandpre |
| 7,026,626 B2 | 4/2006 | Harrison |
| 7,030,999 B2 | 4/2006 | Bischoff et al. |
| 7,031,894 B2 | 4/2006 | Niu et al. |
| 7,046,375 B2 | 5/2006 | Bischoff et al. |
| 7,049,156 B2 | 5/2006 | Kueny |
| 7,053,991 B2 | 5/2006 | Sandusky |
| 7,061,614 B2 | 6/2006 | Wang et al. |
| 7,067,818 B2 | 6/2006 | Harrison |
| 7,068,363 B2 | 6/2006 | Bevis et al. |
| 7,072,050 B2 | 7/2006 | Kimba et al. |
| 7,095,511 B2 | 8/2006 | Chalmers et al. |
| 7,126,131 B2 | 10/2006 | Harrison |
| 7,130,029 B2 | 10/2006 | Wack et al. |
| 7,189,973 B2 | 3/2007 | Harrison |
| 7,196,785 B2 | 3/2007 | Nishiyama et al. |
| 7,242,477 B2 | 7/2007 | Mieher et al. |
| 7,271,394 B2 | 9/2007 | Harrison |
| 7,282,703 B2 | 10/2007 | Walsh et al. |
| 7,342,235 B1 | 3/2008 | Harrison et al. |
| 7,349,079 B2 | 3/2008 | Zhao et al. |
| 7,359,052 B2 | 4/2008 | Fielden et al. |
| 7,391,524 B1 | 6/2008 | Chen et al. |
| 7,394,551 B2 | 7/2008 | Harrison |
| 7,399,975 B2 | 7/2008 | Harrison |
| 7,446,876 B2 | 11/2008 | Harrison |
| 7,485,869 B2 | 2/2009 | Harrison et al. |
| 7,579,601 B2 | 8/2009 | Harrison et al. |
| 2001/0055118 A1 | 12/2001 | Nawracala |
| 2002/0030826 A1 | 3/2002 | Chalmers et al. |
| 2002/0033954 A1 * | 3/2002 | Niu et al. ...................... 356/601 |
| 2002/0088952 A1 | 7/2002 | Rao et al. |
| 2002/0126277 A1 | 9/2002 | Norton et al. |

| | | | |
|---|---|---|---|
| 2002/0149774 A1 | 10/2002 | McAninch | |
| 2002/0154302 A1 | 10/2002 | Rosencwaig et al. | |
| 2002/0190207 A1 | 12/2002 | Levy et al. | |
| 2003/0071996 A1 | 4/2003 | Wang et al. | |
| 2003/0081201 A1 | 5/2003 | Shibata et al. | |
| 2004/0150820 A1 | 8/2004 | Nikoonahad et al. | |
| 2005/0001172 A1 | 1/2005 | Harrison | |
| 2005/0036143 A1 | 2/2005 | Huang | |
| 2005/0088665 A1* | 4/2005 | Bischoff et al. | 356/601 |
| 2006/0001885 A1 | 1/2006 | Hertzsch et al. | |
| 2006/0066855 A1 | 3/2006 | Boef et al. | |
| 2007/0030488 A1 | 2/2007 | Harrison et al. | |
| 2007/0181793 A1 | 8/2007 | Harrison et al. | |
| 2007/0181795 A1 | 8/2007 | Walsh et al. | |
| 2007/0215801 A1 | 9/2007 | Walsh et al. | |
| 2008/0042071 A1 | 2/2008 | Harrison et al. | |
| 2008/0069430 A1* | 3/2008 | Setija et al. | 382/144 |
| 2008/0073560 A1 | 3/2008 | Harrison et al. | |
| 2008/0129986 A1 | 6/2008 | Walsh | |
| 2008/0181793 A1 | 7/2008 | Mistry et al. | |
| 2008/0204710 A1 | 8/2008 | Harrison et al. | |
| 2008/0246951 A1 | 10/2008 | Walsh et al. | |
| 2009/0002711 A1 | 1/2009 | Harrison | |
| 2009/0248074 A1 | 10/2009 | Kliegman et al. | |
| 2010/0051822 A1 | 3/2010 | Harrison | |

FOREIGN PATENT DOCUMENTS

| | | | |
|---|---|---|---|
| JP | 10160572 A | 6/1998 |
| JP | 2003202266 A | 7/2003 |
| JP | 2003232681 A | 8/2003 |
| WO | 9902970 A1 | 1/1999 |
| WO | 2007126612 A2 | 11/2007 |
| WO | 2007130295 A2 | 11/2007 |

OTHER PUBLICATIONS

Lalanne et al, "On The Effective Medium Theory Of Subwavelength Periodic Structures", Journal Of Modern Optics, vol. 43, No. 10, 1996, pp. 2063-2085.

Kinber et al., "Use Of Symmetry In Solving Diffraction Problems", Radio Engineering And Electronic Physics, vol. 16, 1971, pp. 581-587.

Moharam et al., Stable Implementation Of The Rigorous Coupled-Wave Analysis For Surface-Relief Gratings: Enhanced Transmittance Matrix Approach, Optical Society Of America, vol. 12, No. 5, May 1995, pp. 1077-1086.

Moharam et al, "Formulation For Stable And Efficient Implementation Of The Rigorous Coupled-Wave Analysis Of Binary Gratings", Optical Society Of America, vol. 12, No. 5, May 1995, pp. 1068-1076.

Li, "Using Symmetries Of Grating Groove Profiles To Reduce Computation Cost Of The C Method", Optical Society Of America, vol. 24, No. 4, Apr. 2007, pp. 1085-1096.

Tan, "Hybrid-Matrix Algorithm For Rigorous Coupled-Wave Analysis Of Multilayered Diffraction Gratings", Journal Of Modern Optics, vol. 53, No. 4, Mar. 10, 2006, pp. 417-428.

Bai et al., "Group Theoretic Approach To Enhancing The Fourier Model Method For Crossed Gratings With Square Symmetry", Optical Society of America, vol. 23, No. 3, Mar. 2006, pp. 572-580.

Bai et al., "Group Theoretic Approach To The Enhancement Of The Fourier Modal Method For Crossed Gratings: C2 Symmetry Case", Optical Society Of America, vol. 22, No. 4, Apr. 2005, pp. 654-661.

Bai et al., "Reduction Of Computation Time For Crossed Grating Problems: A Group Theoretic Approach", Optical Society Of America, vol. 21, No. 10, Oct. 2004, pp. 1886-1894.

Li, "Use Of Fourier Series In The Analysis Of Discontinuous Periodic Structures", Optical Society Of America, vol. 13, No. 9, Sep. 1996, pp. 1870-1876.

Granet, "Efficient Implementation Of The Coupled Wave Method For Metallic Lamellar Gratings In TM Polarization", Optical Society Of America, vol. 13, No. 5, May 1996, pp. 1019-1023.

Lalanne et al., "Highly Improved Convergence Of The Coupled Wave Method For TM Polarization", Optical Society Of America, vol. 13, No. 4, Apr. 1996, pp. 779-784.

Tan, "Enhanced R Matrix Algorithms For Multilayered Diffraction Gratings", Applied Optics, vol. 45, No. 20, Jul. 10, 2006, pp. 4803-4809.

Kaplan et al., "Characterization Of Bidimensional Gratings By Spectroscopic Ellipsometry And Angle Resolved Mueller Polarimetry", Applied Optics, vol. 43, No. 6, Feb. 20, 2004, pp. 1233-1240.

Novikova et al., "Application Of Mueller Polarimetry In Conical Diffraction For Critical Dimension Measurements In Microelectronics", Applied Optics, vol. 45, No. 16, Jun. 1, 2006, pp. 3688-3697.

Bao, "An Optical Metrology System For Lithography Process Monitoring And Control", Thesis, University of California At Berkeley, Department of Electrical Engineering And Computer Sciences, Spring 2003, pp. 135.

Coulombe et al., "Ellipsometric-Scatterometry For Sub-0.1 µm CD Measurements", SPIE, vol. 3332, 1998, pp. 282-293.

Opsal et al., "Fundamental Solutions For Real-Time Optical CD Metrology", SPIE, vol. 4689, 2002, pp. 163-176.

Bischoff et al., "New Aspects Of Optical Scatterometry Applied To Microtechnology", SPIE, vol. 3215, 1997, pp. 144-155.

Minhas et al., "Towards Sub-0.1µm CD Measurements Using Scatterometry", SPIE, vol. 2725, 1996, pp. 729-739.

Bischoff et al., "Single Feature Metrology By Means For Light Scatter Analysis", SPIE, vol. 3050, 1997, pp. 574-585.

Mills et al., "Spectral Ellipsometry On Patterned Wafers", SPIE, vol. 2637, 1995, pp. 194-203.

Depine et al., "Internal Symmetries In Conical Diffraction From Metallic Gratings", Journal Of Modern Optics, vol. 48, No. 8, 2001, pp. 1405-1411.

Xie et al., "Transmission Of Light Through Periodic Arrays Of Sub-Wavelength Slits In Metallic Hosts", Optics Express, vol. 14, No. 14, Jul. 10, 2006, pp. 6400-6413.

Stephane Robert et al., "Control Of The Homogeneity Of An Optical Grating By A Neural Characterization", Optical Engineering, vol. 44(3), Mar. 2005, 5 pgs.

Tan, "Hybrid-Matrix Algorithm For Rigorous Coupled-Wave Analysis Of Multilayered Diffraction Gratings", Journal Of Modern Optics, vol. 53, No. 4, Mar. 10, 2006, pp. 417-428.

Boyer et al., "Diffraction Theory: Application Of The Fast Fourier Factorization To Cylindrical Devices With Arbitrary Cross Section Lighted In Conical Mounting", Optical Society Of Americas, vol. 23, No. 5, May 2006, pp. 1146-1158.

Bai et al., "Group-Theoretic Approach To Enhancing The Fourier Modal Method For Crossed Gratings With Square Symmetry", Optical Society Of Americas, vol. 23, No. 3, Mar. 2006, pp. 572-580.

Bai et al., "GroupTheoretic Approach To Enhancement Of The Fourier Modal Method For Crossed Gratings: C2 Symmetry Case", Optical Society Of Americas, vol. 22, No. 4, Apr. 2005, pp. 654-661.

Cordeiro et al., "Phase Constraint For The Waves Diffracted By Lossless Symmetrical Gratings At Littrow Mount", Optical Society Of Americas, vol. 23, No. 1, Jan. 2006, pp. 166-171.

Bai et al., "Reduction Of Computation Time For Cross-Grating Problems: A Group-Theorectic Approach", Optical Society Of Americas, vol. 21, No. 10, Oct. 2004, pp. 1886-1894.

Robert et al., "Experimental Characterization Of Subwavelength Diffraction Gratings By An Inverse-Scattering Neural Method", Optical Society Of Americas, vol. 19, No. 12, Dec. 2002, pp. 2394-2402.

Robert et al., "Characterization Of Optical Diffraction Gratings By Use Of A Neural Method", Optical Society Of Americas, vol. 19, No. 1, Jan. 2002, pp. 24-32.

Li, "Symmetries Of Cross-Polarization Diffraction Coefficients Of Gratings", Optical Society Of Americas, vol. 17, No. 5, May 2000, pp. 881-887.

Lalanne, "Improved Formulation Of The Coupled-Wave Method For Two-Dimensional Gratings", Optical Society Of Americas, vol. 14, No. 7, Jul. 1997, pp. 1592-1598.

Logofatu et al., "Identity Of The Cross-Reflection Coefficients For Symmetric Surface-Relief Gratings", Optical Society Of Americas, vol. 16, No. 5, May 1999, pp. 1108-1114.

Zolla et al., "Method Of Fictitious Sources As Applied To The Electromagnetic Diffraction Of A Plane Wave By A Grating In Conical Diffraction Mounts", Optical Society Of Americas, vol. 13, No. 4, Apr. 1996, pp. 796-802.

Peng et al., "Efficient Implementation Of Rigorous Coupled-Wave Analysis For Surface-Relief Gratings", Optical Society Of Americas, vol. 12, No. 5, May 1995, pp. 1087-1096.

Li, "Multilayer Modal Method For Diffraction Gratings Of Arbitrary Profile, Depth And Permittivity", Optical Society Of Americas, vol. 10, No. 12, Dec. 1993, pp. 2581-2591.

Li et al., "Convergence Of The Coupled-Wave Method For Metallic Lamellar Diffraction Gratings", Optical Society Of Americas, vol. 10, No. 6, Jun. 1993, pp. 1184-1189.

Peng, "Rigorous Formulation Of Scattering And Guidance By Dielectric Grating Waveguides: General Case Of Oblique Incidence", Optical Society Of Americas, vol. 6, No. 12, Dec. 1989, pp. 1869-1883.

Moharam et al., "Rigorous Coupled-Wave Analysis Of Grating Diffraction-E-mode Polarization And Losses", Optical Society Of Americas, vol. 73, No. 4, Apr. 1983, pp. 451-455.

Moharam et al., "Diffraction Analysis Of Dielectric Surface-Relief Gratings", Optical Society Of Americas, vol. 72, No. 10, Oct. 1982, pp. 1385-1392.

Moharam et al., "Rigorous Coupled-Wave Analysis Of Planar-Grating Diffraction", Optical Society Of Americas, vol. 71, No. 7, Jul. 1981, pp. 811-818.

Knop., "Rigorous Diffraction Theory For Transmission Phase Gratings With Deep Rectangular Grooves", Optical Society Of Americas, vol. 68, No. 9, Sep. 1978, pp. 1206-1210.

Kong, "Second-Order Coupled-Mode Equations For Spatially Periodic Media", Optical Society Of America, vol. 67, No. 6, Jun. 1977, pp. 825-829.

Azzam et al., "Generalized Ellipsometry For Surfaces With Directional Preference: Application To Diffraction Gratings", Journal Of The Optical Society Of America, vol. 62, No. 12, Dec. 1972, pp. 1521-1530.

Case, "Coupled-Wave Theory For Multiply Exposed Thick Holographic Gratings", Journal Of The Optical Society Of America, vol. 65, No. 6, Jun. 1975, pp. 724-729.

Kaspar, "Diffraction By Thick, Periodically Stratified Gratings With Complex Dielectric Constant", Journal Of The Optical Society Of America, vol. 63, No. 1, Jan. 1973, pp. 37-45.

Azzam et al., "Application Of Generalized Ellipsometry To Anisotropic Crystals", Journal Of The Optical Society Of America, vol. 64, No. 2, Feb. 1974, pp. 128-133.

Bruckhardt, "Diffraction Of A Plane Wave At A Sinusoidally Stratified Dielectric Grating", Journal Of The Optical Society Of America, vol. 56, No. 11, Nov. 1966, pp. 1502-1509.

Krukar et al., "Reactive Ion Etching Profile And Depth Characterization Using Statistical And Neural Network Analysis Of Light Scattering Data", American Institute Of Physics, vol. 74(6), Sep. 15, 1993, pp. 3698-3706.

Li, "A Modal Analysis Of Lamellar Diffraction Gratings In Conical Mountings", Journal Of Modern Optics, vol. 40, No. 4, 1993, pp. 553-573.

Momeni et al., "Pure Coupled Mode Analysis Of Diffraction By Isotropic Transmission Volume Gratings", IEEE Transactions On Antennas And Propagation, vol. 52, No. 12, Dec. 2004, pp. 3304-3311.

Momeni et al., "Improved Coupled Wave Analysis Of Two-Dimensional Planar Multiple Gratings", IEEE Transactions On Antennas And Propagation, vol. 52, No. 1, Jan. 2004, pp. 165-171.

Tan, "Enhanced R-matrix Algorithms For Multilayered Diffraction Gratings", Applied Optics, vol. 45, No. 20, Jul. 10, 2006, pp. 4803-4809.

Novikova et al., "Application Of Mueller Polarimetry In Conical Diffraction For Critical Dimension Measurements In Microelectronics", Applied Optics, vol. 45, No. 16, Jun. 1, 2006, pp. 3688-3697.

Garnaes et al., "Profiles Of A High-Aspect-Ratio Grating Determined By Spectroscopic Scatterometry And Atomic-Force Microscopy", Applied Optics, vol. 45, No. 14, May 10, 2006, pp. 3201-3212.

Kallioniemi et al., "Characterization Of Diffraction Gratings In A Rigorous Domain With Optical Scatterometry: Hierarchical Neural-Network Model", Applied Optics, vol. 38, No. 28, Oct. 1, 1999, pp. 5920-5930.

Ahmed et al., "Comparison Of Beam Propagation Method And Rigorous Coupled-Wave Analysis For Single And Multiplexed Volume Gratings", Applied Optics, vol. 35, No. 22, Aug. 1, 1996, pp. 4426-4435.

Minhas et al., "Ellipsometric Scatterometry For The Metrology Of Sub-01-μm-linewidth Structures", Applied Optics, vol. 37, No. 22, Aug. 1, 1998, pp. 5112-5115.

Kallioniemi et al, "Optical Scatterometry Of Subwavelength Diffraction Gratings: Neural-Network Approach", Applied Optics, vol. 37, No. 25, Sep. 1, 1998, pp. 5830-5835.

Huang et al., "Normal-Incidence Spectroscopic Ellipsometry For Critical Dimension Monitoring", Applied Physics Letters, vol. 78, No. 25, Jun. 18, 2001, pp. 3983-3985.

Press et al., "Numerical Recipes In C" The Art Of Scientific Computing, Second Edition, 1992, 15.5 Nonlinear Models, pp. 681-688.

Harrison et al., Copending U.S. Appl. No. 11/600,477, "Contamination Monitoring And Control Techniques For Use With An Optical Metrology Instrument", Filed Nov. 16, 2006, 53 pgs.

U.S. Appl. No. 12/834,939 Official Action dated Oct. 29, 2010.

Das at al., "Image Evaluation of the High-Resolution VUV Spectrometer at SURF II by Ray Tracing" Journal of Research of the National Institute of Standards and Technology, vol. 103, No. 5, pp. 483-495, Sep.-Oct. 1998.

US Re-Examination U.S. Appl. No. 90/009,409 Official Action dated Jun. 18, 2010.

Chinese Patent Application No. 200480027513.6 Official Action dated Jul. 18, 2008.

US Re-Examination U.S. Appl. No. 90/009,320 Official Action dated Sep. 25, 2009, and Notice of Intent to Issue Re-Exam Certificate dated Jun. 23, 2010.

Aspnes, D.E., "Determination of Optical Properties by Ellipsometry", Handbook of Optical Constants of Solids, vol. 1, pp. 104-108, Academic Press, 1998.

Bloomstein et al., "Contamination Rates of Optical Surface at 157nm in the Presence of Hydrocarbon Impurities", Optical Microlithography XV, Proceedings of the SPIE, vol. 4691, pp. 709-723, Jul. 30, 2002.

Field et al., "Method of Using the Reflectance Ratios of Difference Angles of Incidence for the Determination of Optical Constants", Applied Optics, vol. 10, No. 6, pp. 1402-1405, Jun. 1971.

Hunter, W., "Errors in Using the Reflectance vs Angle of Incidence Method for Measuring Optical Constants", Journal of the Optical Society of America, vol. 55, No. 10, part 1, pp. 1197-1204, Oct. 1965.

Hunter et al., "Thickness of Absorbing Films Necessary to Measure Their Optical Constants Using the Reflectance—Vs—Angle—Of—Incidence Method", Journal of the Optical Society of America, vol. 64, No. 4, pp. 429-433, Apr. 1974.

Jellison et al., "Parameterization of the Optical Functions of Amorphous Materials in the Interband Region", Applied Physics Letter, Jul. 15, 1996 (vol. 69, No. 3, pp. 371-373), and Sep. 30, 1996 (vol. 69, No. 14, pp. 2137).

Okoroanyanwu et al.. "Contamination Monitoring and Control on ASML MS-VII 157nm Exposure Tool", Optical Microlithography XVII, Proceedings of the SPIE, vol. 5377, pp. 1695-1707, May 28, 2004.

International Application PCT/US2004/030859 Search Report dated Feb. 24, 2005.

Rivas, C., "Optical Characterization of Hafnium-Based High-K Dielectric Films Using Vacuum Ultraviolet Reflectometry", Proceedings of the XV International Conference on Vacuum Ultraviolet Radiation Physics, Berlin, Germany Jul. 29-Aug. 3, 2007.

International Application PCT/US2007/010003 Search Report issued Dec. 17, 2008.

U.S. Appl. No. 10/930,339 Official Action dated Sep. 29, 2009.
U.S. Appl. No. 10/930,339 Official Action dated Jan. 18, 2007.
U.S. Appl. No. 10/930,339 Official Action dated Sep. 6, 2007.
U.S. Appl. No. 10/930,339 Official Action dated Apr. 18, 2008.
U.S. Appl. No. 10/930,339 Official Action dated Nov. 13, 2008.
U.S. Appl. No. 12/454,837 "Automated Calibration Methodology for VUV Metrology System" filed on May 22, 2009.

Visentine, J., "Optical Characterization of Molecular Contaminant Films", Photonics Tech Briefs, Jan. 1, 2007.

U.S. Appl. No. 12/592,641 Official Action dated Aug. 20, 2010.

Japanese Patent Application # 528098/06 Official Action dated Jun. 15, 2010 (including English translation).

US Re-Examination U.S. Appl. No. 95/000,535 Official Action dated May 14, 2010.

Acton Research Corporation, "Acton Research Purged CAMS Optical Measurement System", Acton Research Product Brochure, USA, Published prior to Sep. 23, 2003.

McPherson Inc., "Reflectometer for Sample Analysis", McPherson Product Brochure, USA, Published prior to Sep. 23, 2003.

McPherson Inc., "Spectral Reflectometer", McPherson Product Brochure, USA, Nov. 12, 2001.

McPherson Inc., "VUVaS Spectrophotometers for 115 nm to >380nm", McPherson Product Brochure, USA, published prior to Sep. 23, 2003.

McPherson Inc., "VUVaS Spectrophotometers, Made to Measure 115-380 nm", McPherson Product Brochure, USA, published prior to Sep. 23, 2003.

Rubloff, G.W., "Surface Reflectance Spectroscopy System", Technical Disclosure, IP.COM, May 1, 1977.

Sopra., "SE and GXR combined on the same instrument", printed from www.sopra-sa.com on Feb. 19, 2002.

Sopra., "The Ideal Thin Film Characterization Unit for Development and Pilot Line Environment", printed from www.sopra-sa.com on Feb. 19, 2002.

Sopra., "The Thin Film Tool for Next Generation Lithography at 157 nm", printed from www.sopra-sa.com on Feb. 19, 2002.

U.S. Appl. No. 12/854,917 "Method and Apparatus For Accurate Calibration of VUV Reflectometer" filed on Aug. 12, 2010.

U.S. Appl. No. 12/876,242 "Broad Band Referencing Reflectometer" filed on Sep. 7, 2010.

Sentech Instruments GMBH., "Vacuum UV Spectroscopic Ellipsometers", printed from www.sentech.de on Feb. 20, 2002.

J.A. Woolam Company, "Award Winning VUV-Vase is the latest addition to our line of Spectroscopic Ellipsometers", printed from www.jawoolam.com on Nov. 5, 2002.

Request for Ex Parte Reexamination for US Patent # 7,067,818 filed Feb. 11, 2009

Request for Ex Parte Reexamination for US Patent # 7,067,818 filed Feb. 12, 2010.

Request for Ex Parte Reexamination for US Patent # 7,026,626 filed Nov. 7, 2008.

U.S. Appl. No. 12/834,939 "Combined optical metrology techniques" filed on Jul. 13, 2010.

U.S. Appl. No. 12/844,851 "Method and System for Using Reflectometry Below DUV Wavelengths For Measuring Properties" filed on Jul. 28, 2010.

U.S. Appl. No. 12/876,242 Official Action dated Nov. 19, 2010.

U.S. Appl. No. 12/590,151 Official Action dated Mar. 17, 2011.

U.S. Appl. No. 12/876,242 Official Action dated May 20, 2011.

U.S. Appl. No. 12/834,939 Official Action dated Jun. 10, 2011.

* cited by examiner

FIG. 1 - (Prior Art)

METHOD AND APPARATUS FOR OPTICALLY MEASURING PERIODIC STRUCTURES USING ORTHOGONAL AZIMUTHAL SAMPLE ORIENTATION

This application is a continuation of U.S. patent application Ser. No. 11/998,263 filed on Nov. 29, 2007 now abandoned which claims priority to Provisional Patent Application No. 60/872,010 filed Nov. 30, 2006; the disclosure of which is expressly incorporated herein by reference in its entirety.

TECHNICAL FIELD OF THE INVENTION

This invention relates to an optical metrology apparatus and methods and systems for measuring periodic structures using multiple incident azimuthal (phi) and polar (theta) angles, and particularly to enhanced calculation speed for a special case of phi=90 incidence for 1-D (line and space) gratings, having an incident plane parallel to grating lines. This results in additional datasets to supplement data collected in the phi=0 classical mount configuration without an untenable increase in computation cost.

BACKGROUND OF THE INVENTION

A widely referenced source on a rigorous coupled wave (RCW) algorithm is that of Moharam and Gaylord (M. G. Moharam, E. B. Grann, D. A. Pommet, and T. K. Gaylord, J. Opt. Soc. Am. A, Vol. 12, No. 5, p. 1068 (1995)). A schematic from their paper showing the diffraction problem is reproduced in FIG. 1. In particular, FIG. 1 defines the various incident conditions for the diffraction problem. The plane of incidence is defined by the polar angle, theta, and the azimuthal angle, phi. The azimuthal angle defines the angle the incident plane makes with the plane perpendicular to the grating lines, so that phi=0 corresponds to the classical incidence case. The angle psi defines the direction of the electric field with respect to the plane of incidence, with psi=90 corresponding to s polarized and psi=0 to p polarized incident light.

As shown in FIG. 1, a diffraction grating 100 has a grating region 104 formed in a substrate 102 (the substrate being designated as Region II). The grating region 104 has a height d as indicated in the figure. Region I is comprised of the material above the grating region, in this case in air or vacuum space. As indicated in FIG. 1, the grating region may be formed of alternating grating lines 106 and grating spaces 108. The grating lines 106 may have a width 109. The grating periodicity is characterized by the grating period 110 as indicated.

It will be recognized that a diffraction grating may be formed in other manners than that of FIG. 1 and that FIG. 1 is only one exemplary diffraction grating as known to those skilled in the art. For example, a diffraction grating need not be formed utilizing spaces. FIG. 1B shows one such alternative diffraction grating. As shown in FIG. 1A, the diffraction grating 100 may be comprised of grating lines 106A and 106B, again having a grating region 104 with height d. In this example, grating lines 106A and 106B will be formed in a manner in which the lines have different optical properties. Further, though the examples shown include gratings having two different optical properties within each period of the diffraction grating, it will be recognized that the diffraction grating may comprise three or more different materials within each period. Likewise, though each grating line is shown as a single material, it will be recognized that the grating lines may be formed of multiple layers of the same or different materials. In addition, though the grating lines are shown as being "squared off," it will be recognized that each line may have sloped sides, curved edges, etc.

With reference again to FIG. 1, an x-y-z coordinate system is shown having a frame of reference in which the x-direction is shown as being perpendicular to the original alignment of the grating lines. The plane of incidence 112 of the incident light is defined by the polar angle 114, theta and the azimuthal angle 116, phi. The electric field 120 has a propagation vector 122 ($k$) of the incident wave. The unit vectors 124 ($t$) and 126 ($n$) are tangent and normal to the plane of incidence, respectively. As mentioned above, the angle 128, psi, defines the direction of the electric field with respect to the plane of incidence.

The RCW method involves the expansion of the field components inside and outside the grating region in terms of generalized Fourier series. The method consists of two major parts—an eigen-problem to determine a general solution inside the grating layer, and a boundary problem to determine the reflected and transmitted diffracted amplitudes along with the specific solution for the fields inside the grating region. The Fourier series are truncated after a finite number of terms. The truncation is usually characterized by the truncation order, N, which means that 2N+1 spatial harmonics are retained in the series (positive and negative terms to ±N, and the 0 term).

Standard methods for solving the eigen-problem, boundary problem, and the various other matrix multiplications and inversions involved are order $N^3$ operations. This means that an increase of the truncation order by a factor of two results in an increase in overall computation time by a factor of approximately 8. The truncation order required for convergence is determined by the specifics of the diffraction problem, and generally increases for larger pitch to incident wavelength ratios and larger optical contrast between grating lines and spaces. The result is that while some diffraction problems are very tenable, others quickly become impractical to solve due to a large computation cost.

In the case of the phi=0 classical mount, the diffraction problem decouples into TE and TM components, which can be solved separately (for the phi=0 mount, TE polarization corresponds to s polarized incident light, and TM polarization corresponds to p polarized incident light). Any arbitrary polarization is decomposed into a combination of the TE and TM problems. In practice, the incident light is often purely TE or TM polarized, and only one case needs to be solved. For given truncation order N and classical mount the eigen-problem is of size 2N+1, and the boundary problem is of size 2(2N+1).

The general case where phi≠0 is known as conical diffraction. In this case, the s and p components are coupled, with a corresponding increase in the amount of computation time. The boundary problem involves 4(2N+1) sized matrices. The eigen-problem has been successfully decoupled into two smaller eigen-problems, each of size 2N+1 (see Moharam and Gaylord 1995 referenced above, or S. Peng and G. M. Morris, J. Opt. Soc. Am. A, Vol. 12, No. 5, p. 1087 (1995)). Therefore, the computation time for the general conical incidence case suffers a factor of 2 increase for the eigen-problem and a factor of 8 increase for the boundary problem compared to the corresponding classical mount case with same polar incident angle, theta.

Analysis of a diffraction grating problem is of particular use to determining the various characteristics of the diffraction grating structure. For example, critical dimensions of a device (such as in semiconductor processing in one exemplary use) may be monitored by evaluating the characteristics of a diffraction grating as is known in the art. By evaluating data from known optical metrology tools using regression and/or library methods, the diffraction analysis may lead to, for example, a determination of the grating line widths, the grating height/depth, the period of the grating, the slopes and profiles of the grating, the material composition of the grating, etc. As known in the art, such grating characteristics may be related to the characteristics of a device that is being analyzed, such as for example but not limited to widths, heights, depths, profiles, etc. of transistors, metallization lines, trenches, dielectric layers, or the like, all as is known to those skilled in the art. Since the regression and/or library methods may require many calculations of diffraction efficiencies, special consideration must be given to computation expense in such applications.

SUMMARY OF THE INVENTION

An optical metrology apparatus for measuring periodic structures using multiple incident azimuthal (phi) and polar (theta) incident angles is described. One embodiment provides the enhanced calculation speed for the special case of phi=90 incidence for 1-D (line and space) structures, which has the incident plane parallel to the grating lines, as opposed to the phi=0 classical mounting, which has incident plane perpendicular to the grating lines. The enhancement reduces the computation time of the phi=90 case to the same order as the corresponding phi=0 case, and in some cases the phi=90 case can be significantly faster. One advantageous configuration consists of two measurements for each sample structure, one perpendicular to the grating lines and one parallel. This provides additional information about the structure, equivalent to two simultaneous angles of incidence, without excessive increase in computation time. Alternately, in cases where the computation for phi=90 is faster than the corresponding phi=0 incidence, it may be advantageous to measure parallel to the grating lines only. In the case where two sets of incident angles are used, the incident light can be polarized to provide a total of four sets of data—$R_s^0$, $R_p^0$, $R_s^{90}$, $R_p^{90}$—for each incident polar angle, all from the same structure ($R_s^0$ being a data set having incident phi=0 and incident polarization normal to the plane of incidence, $R_p^{90}$ being a data set having incident phi=90 and incident polarization within the plane of incidence, etc.).

In one embodiment, the techniques described herein provide an optical metrology apparatus and methods and systems for measuring periodic structures using multiple incident azimuthal (phi) and polar (theta) angles, and particularly to enhanced calculation speed for a special case of phi=90 incidence for 1-D (line and space) structures, having an incident plane parallel to grating lines.

In one embodiment, a method of reducing an RCW calculation for the phi=90 incidence mount by exploiting the degeneracy in the resulting diffraction problem is provided. The method may include using this calculation in the regression part of an optical grating measurement. Alternately, the method may include using the enhanced speed in the generation of a database library to be used in conjunction with an optical grating measurement. The optical method could be any in existence, such as reflectometry, polarized reflectometry, ellipsometry, polarimetry, etc. and can be broadband or single wavelength.

The method may include illuminating a grating structure with polarized or unpolarized, monochromatic or broadband light. The incident light may be at one or more polar angles, theta, at the phi=0 and phi=90 azimuthal directions for each of the polar angles. The method may further include detecting the response, for a total of up to four datasets per grating sample per incident polar angle, which are then simultaneously analyzed in order to take advantage of the enhanced information content contained in the multiple datasets. The calculation time is reduced compared to conventional RCW formulations due to the reduced calculation requirements for the phi=90 cases.

One or more diffracted orders may be detected along with or instead of the 0'th order. Further when the detected response is reflected or diffracted intensity, one or more of the datasets may be used to normalize the other datasets, making an absolute calibration of the tool unnecessary.

One or more of the datasets may be used to normalize the other datasets, making an absolute calibration of the optical tool unnecessary, and the inverse ratio is substituted in calculations for specific wavelength regions where the denominator of the original ratio is near zero.

One or more of the datasets may be used to normalize the other datasets, making an absolute calibration of the tool unnecessary, and the inverse ratio is substituted in calculations for specific wavelength regions where the denominator of the original ratio is near zero, and a weighting function is used to equalize the contribution to the merit function regardless of reflectance ratio magnitude.

In addition, one or more of the datasets may be used to normalize the other datasets, making an absolute calibration of the optical tool unnecessary, and the data regions where the denominator of the ratio is near zero are dropped from the analysis.

Data collected from the diffracting structure may be normalized by data from a nearby uniform film structure having the same stack layer structure as the diffracting structure.

The angle of incidence may be explicitly varied by changing the polar angle of incidence of the optical plane, or by rotating the optical plane or sample at fixed polar angle to generate phi=0 and phi=90 incident data.

The multiple angle of incidence data may be generated through use of a high numerical aperture optic (so it contains a spread of angles) and selecting specific angles using an aperture stop to allow light incident at only specific angles.

In addition, multiple angles of incidence may be allowed, and the data simultaneously analyzed.

Further, the method may include only measuring and analyzing the phi=90 incidence data.

As described below, other features and variations can be implemented, if desired, and a related method can be utilized, as well.

DESCRIPTION OF THE DRAWINGS

It is noted that the appended drawings illustrate only exemplary embodiments of the invention and are, therefore, not to be considered limiting of its scope, for the invention may admit to other equally effective embodiments.

FIG. 1 shows a schematic diagram of diffraction problem illustrating polar (theta) and azimuthal (phi) incident angles.

DETAILED DESCRIPTION OF THE INVENTION

Figure 1B:
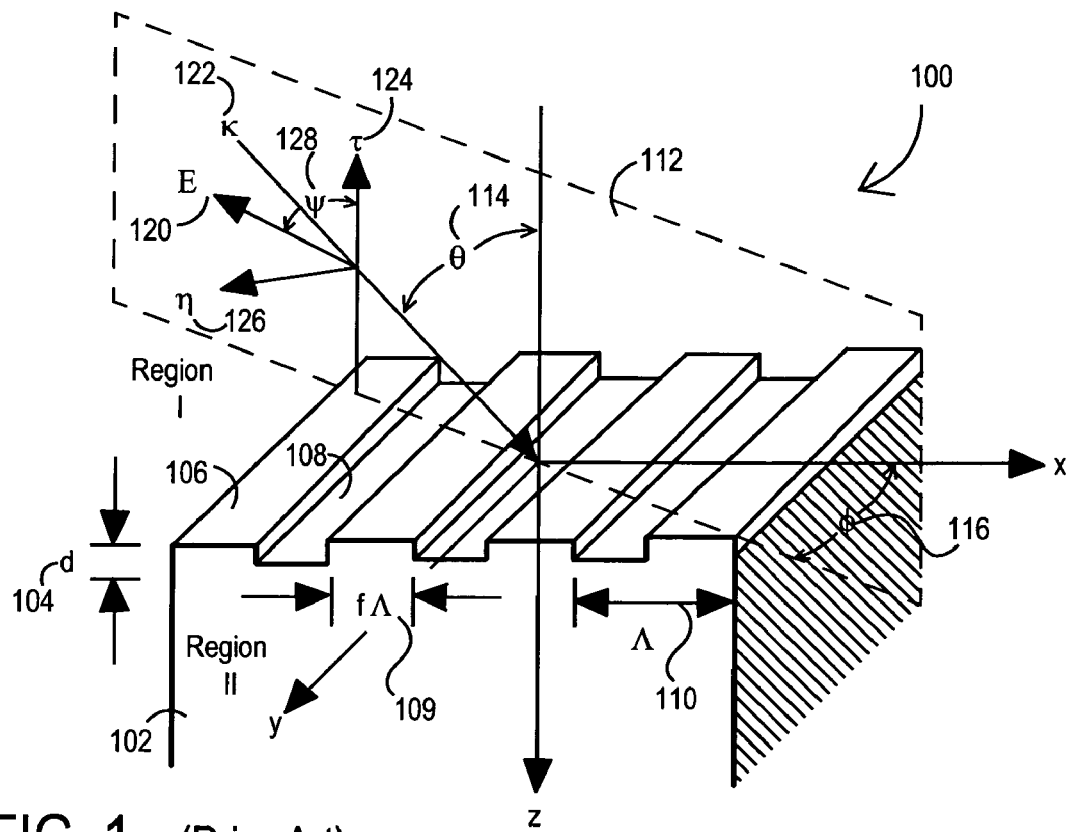
FIG. 1B shows an exemplary alternative diffraction grating.

One way to directly attack the time required for the RCW method is to reduce the number of spatial harmonics involved in the eigen-problem, the boundary problem, or both. This was done for the general case to a large extent in the work of Moharam and Gaylord in their papers: M. G. Moharam, E. B. Grann, D. A. Pommet, and T. K. Gaylord, "Formulation for stable and efficient implementation of the rigorous coupled-wave analysis of binary gratings," J. Opt. Soc. Am. A 12, 1068-1076 (1995) and M. G. Moharam, D. A. Pommet, E. B. Grann, and T. K. Gaylord, "Stable implementation of the rigorous coupled-wave analysis for surface-relief gratings: enhanced transmittance matrix approach," J. Opt. Soc. Am. A 12, 1077-1086 (1995). Subsequent modifications to enhance the TM convergence have included those techniques shown in: P. Lalanne and G. M. Morris, "Highly improved convergence of the coupled-wave method for TM polarization," J. Opt. Soc. Am. A 13, 779-784 (1996); G. Granet and B. Guizal, "Efficient implementation of the coupled-wave method for metallic lamellar gratings in TM polarization," J. Opt. Soc. Am. A 13, 1019-1023 (1996); and L. Li, "Use of Fourier series in the analysis of discontinuous periodic structures," J. Opt. Soc. Am. A 13, 1870-1876 (1996). However, for certain incidence conditions where the incident plane wave has an x-periodicity that is the same as or is a multiple of the grating period, the diffraction problem benefits from additional degeneracy, and the coupled equations can be even further reduced.

One case where this occurs is when the plane of incidence is in the phi=90 mount so that the incident wave is constant with x, and the resulting degeneracy can be exploited to reduce the total number of unknowns. This reduces the total number of spatial harmonics required for the conical diffraction case from 4(2N+1) to 4(N+1). The result is a reduction of the computation time required by a factor of approximately 8 compared to the standard phi=90 conical diffraction case. In addition, a small but significant reduction in computation time compared to the classical mount with same theta is achieved. There are still two eigen-problems, but each of size N+1, leading to an overall reduction of the eigen-problem by a factor of approximately 4 compared to the comparable phi=0 case. The boundary problems for the two cases require approximately the same computation time (2(2N+1) vs. 4(N+1) matrix sizes). Therefore, the computation time for the phi=90 case is reduced to the same order as the corresponding phi=0 case. The phi=90 case can sometimes be significantly faster than the phi=0 case, depending on how much influence the eigen-problem has on the overall computation time. The result is that the additional azimuthal angle phi=90 can be added to the data without an excessive increase in computation time. It will be recognized that although the concepts described herein may refer to analysis at particular angles such as phi=0 and phi=90, the concepts are not limited to use of these exact angles. For example, equipment and sample tolerances may result in other angles being actually used as variability from an anticipated angle is to be expected in real world applications. In addition, variations from the angles of best choice may be purposefully allowed beyond such tolerances while still obtaining the benefits of the techniques described herein. For example, the optical system and grating may be of such a nature that variations from the most desirable angles will still provide a sufficiently accurate calculation at other angles such that the data collected and the calculations may be effectively similar to the use of phi=0 and phi=90 to the extent that sufficient accuracy for a particular application is obtained. In this manner angles that deviate from the phi=0 and phi=90 may be considered to be effectively phi=0 and phi=90 for the purpose of utilizing a metrology tool implementing the techniques described herein for a given application.

An effective way of increasing the amount of information that can be extracted from a single sample is to collect more data sets. This is often done by using multiple angles of incidence theta or, in the case of grating structures, using multiple azimuthal angles. For instance, T. Novikova, A. De Martino, S. B. Hatit, and B. Drevillon, "Application of Mueller polarimetry in conical diffraction for critical dimension measurements in microelectronics," Appl. Opt. 45, 3688-3697 (2006) shows a technique to extract more information about grating line-shapes using multiple azimuthal angles in conjunction with Mueller polarimetry.

This is significant since the hardware implementation for multiple phi configurations is considerably simpler than cases where multiple polar angles are used. In the simplest case, a fixed angle theta can be used, while the sample or stage is rotated through the azimuths. Alternately, the optic objective could be rotated. To take advantage of the above mentioned RCW improvements, the system would simply have to rotate the stage/sample/objective by 90 degrees and back for each measurement (FIGS. 2A-2B), generating two datasets for each sample, at orthogonal incident conditions.

Figure 2A:
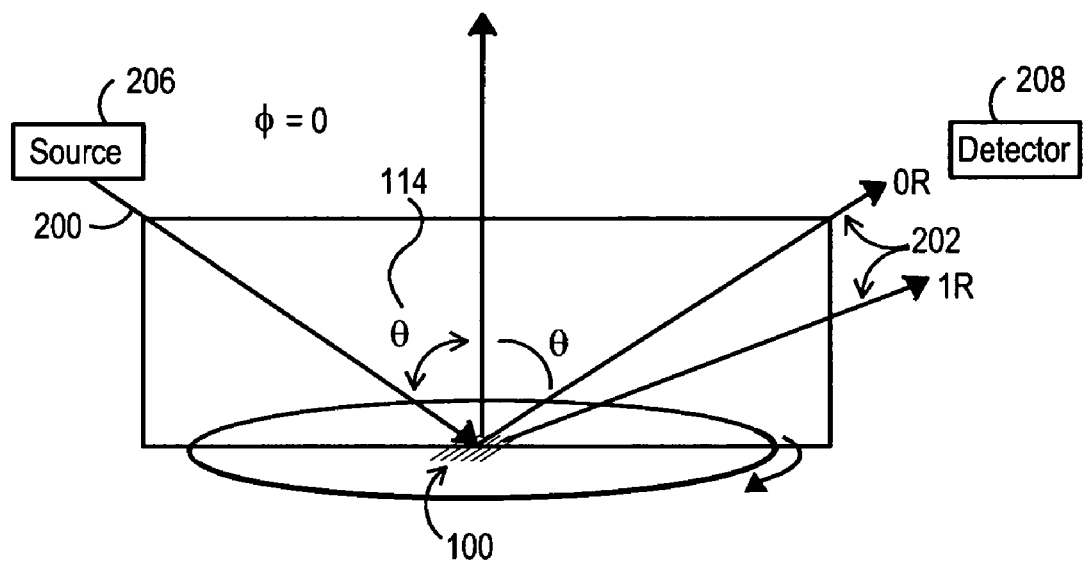
FIGS. 2A and 2B shows rotation of the stage/sample/objective by 90 degrees and back for each measurement.

As shown in FIG. 2A, a substrate is provided with a diffraction grating 100. A source 206 provides an incident light wave 200 at a polar angle 114 (theta) and an azimuthal angle 116 (phi). As shown in FIG. 2A phi=0 so no angle is indicated. A detector 208 may be provided to detect the diffracted orders of reflected light 202. As used herein, light detected from a diffraction grating may be referred to as reflected light, reflected data, or the like and may include one or both of specular reflection of the zero order light and higher order diffracted light.

Figure 2B:
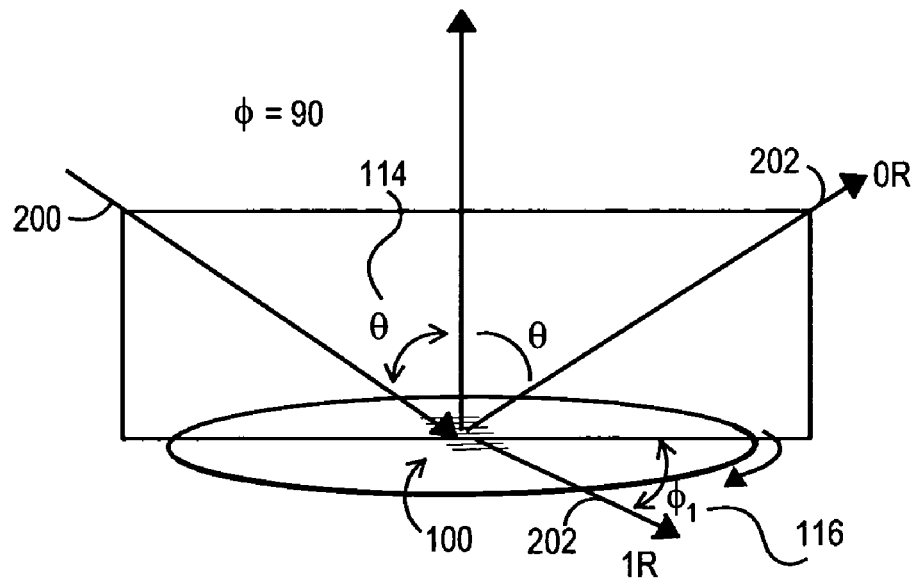

Though not shown in the figures provided herein, a computer system, processor, or the like may be coupled to the detector to process the collected data according to the analysis techniques described herein. The rotation of the diffraction grating with reference to the position of FIG. 2A is shown in FIG. 2B. As shown in FIG. 2B, the diffraction grating has been rotated (for example by rotating the stage, the sample, or the incident light or a combination thereof) so as to create an azimuthal angle 116 (phi) that is phi=90.

Figure 3A:
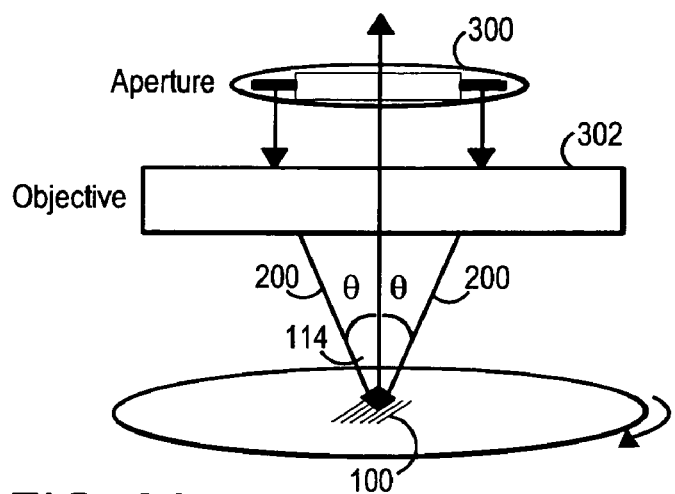
FIGS. 3A-3E illustrate using a high NA objective with an aperture stop that allows light incident at specific angles. Multiple incident angles are achieved by rotating the sample, aperture, or objective. One modification might simultaneously illuminate the grating from both directions (phi=0 and phi=90) as shown in FIG. 3D and FIG. 3E.
Figure 3B:
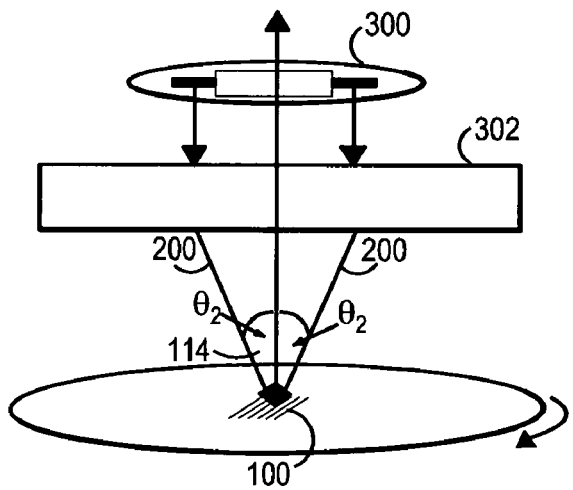
Figure 3C:
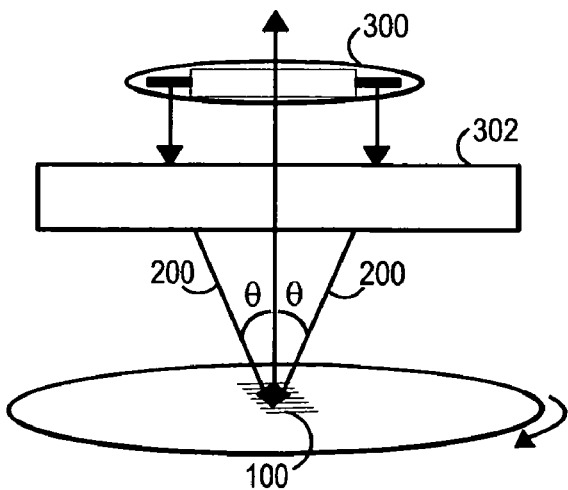

Another means for collecting data at multiple angles of incidence could utilize the large cone angle inherent in high numeric aperture (NA) normal incident objective systems in conjunction with an aperture stop to allow light incident at specific angles, as shown in FIGS. 3A-C. One advantage of this configuration is that multiple polar angles can be more easily incorporated, in addition to the orthogonal azimuthal angles. As shown in FIG. 3A an aperture 300 provides collimated light to an objective 302 which focuses the light on a diffraction grating 100 at a polar angle 114 theta. Different aperture settings are shown between FIGS. 3A and 3B to illustrate utilizing different polar angles theta. As shown in FIGS. 3A and 3B, the incident wave is not rotated from the classical phi=0 orientation. FIG. 3C illustrates a rotation such that phi does not equal zero, for example phi=90.

Figure 3E:
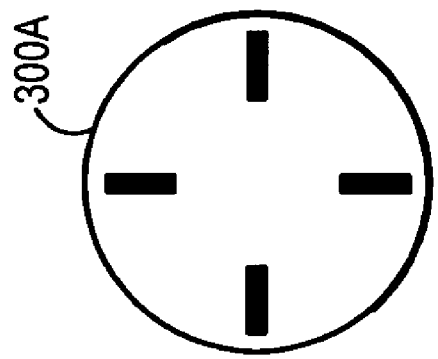
Figure 3D:
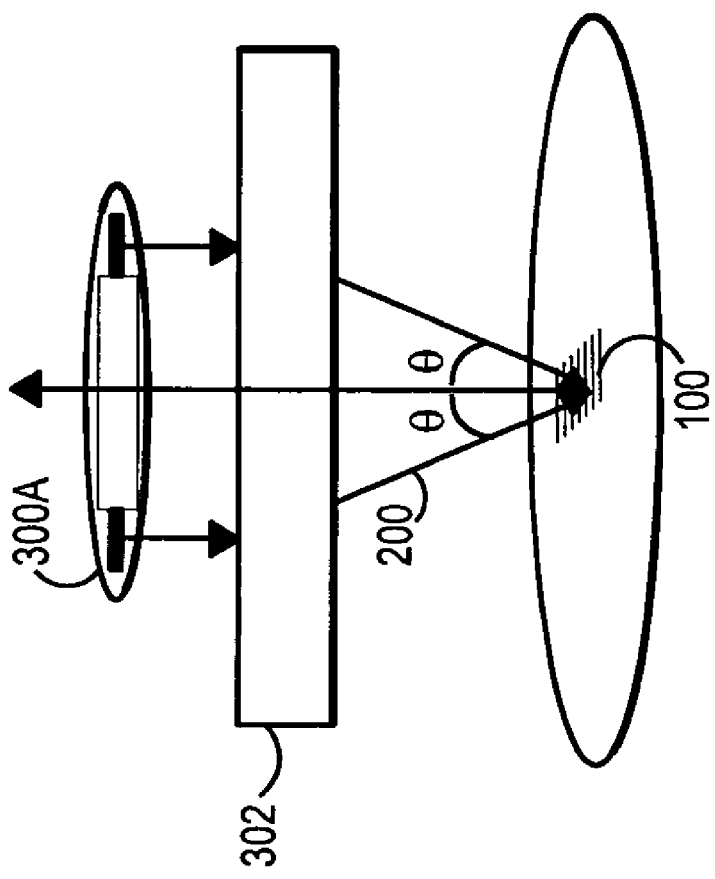

Another possibility might simultaneously illuminate the sample from both directions (phi=0 and phi=90). This could be implemented using two separate, orthogonal optic planes, or a modified version of the high NA system (FIG. 3D). The configuration of FIG. 3D is similar to that of FIG. 3A except a modified aperture 300A is provided. A top view of the modified aperture 300A is shown in FIG. 3E. As can be seen, the aperture 300A allows for light to pass in multiple directions, more particularly in a manner such that phi=0 and phi=90 may be simultaneously illuminated.

It will be recognized by those in the art that the embodiments of FIGS. 2A-2B and 3A-3D are merely illustrative so as to demonstrate the technique of changing the azimuthal angle. A wide range of optical metrology tool configurations may be utilized to achieve the desired incidence conditions so as to acquire the data sets described herein. These data sets may then be utilized in a manner that yields desired characteristics of a diffraction grating from the reduced computational complexity analysis that is achieved by collecting the rotated data as described in more detail below. It will also be recognized that although the present disclosure generally is described in reference to data collected at two phi angles (phi=0 and 90 angles), the techniques described herein are not limited to such techniques. In particular, the techniques described herein provide a reduced computation technique that may be utilized for measurements collected at a single phi angle. Further, additional phi angles beyond two may also be utilized to collect data while still obtaining the benefits described herein. Thus, the concepts described herein are not merely limited to collection of data at two phi angles.

Note that collecting multiple broadband datasets using different azimuthal incidence conditions is distinct from the old method of "phi scatterometry", where the entire dataset consists of the diffraction spectrum of a single wavelength as a function of the azimuthal angle, phi.

The light can additionally be polarized parallel and perpendicular to the plane of incidence, so that four simultaneous data sets per incident theta can be obtained for a given 1-D grating structure, with corresponding enhancement in information. Alternately, each of the four configurations can be explored for a particular structure, and the most promising configuration employed in practice for measuring that particular structure.

Further, the additional datasets may enhance the information content to the extent that fewer wavelengths in a broadband system can be used in the analysis, and in this way the measurement can actually be made faster than a single angle of incidence configuration broadband measurement. In other words, the total number of calculations with respect to incident conditions, including wavelength and angle, may be reduced over that required for a single incident condition over many more wavelengths, while still extracting the same information about the grating structure.

Another advantageous configuration is to collect and analyze the ratio of reflected (0 order, for instance) intensity from the phi=0 scan to that of the reflected (0 order) intensity of the phi=90 scan. The intensity ratio is the same as the reflectance ratio, as long as the intensities are measured in quick succession so that there is minimal system drift between the two measurements. In this way the system calibration can be skipped, and the intensity ratio can be analyzed according to the above methods, taking advantage of the reduction in computation expense for the phi=90 case. In some wavelength ranges, the denominator may be close to zero. Those regions need not be analyzed, or the inverse ratio can be analyzed instead. This implementation can be particularly advantageous when using Vacuum Ultra-Violet (VUV) incident light. One implementation of a VUV metrology apparatus is described in U.S. Pat. No. 7,126,131, Broad Band Referencing Reflectometer, by Harrison, the disclosure of which is incorporated herein by reference in its entirety. For such systems, contaminant buildup on calibration standards over time causes difficulties for traditional calibration methods.

Figure 4:
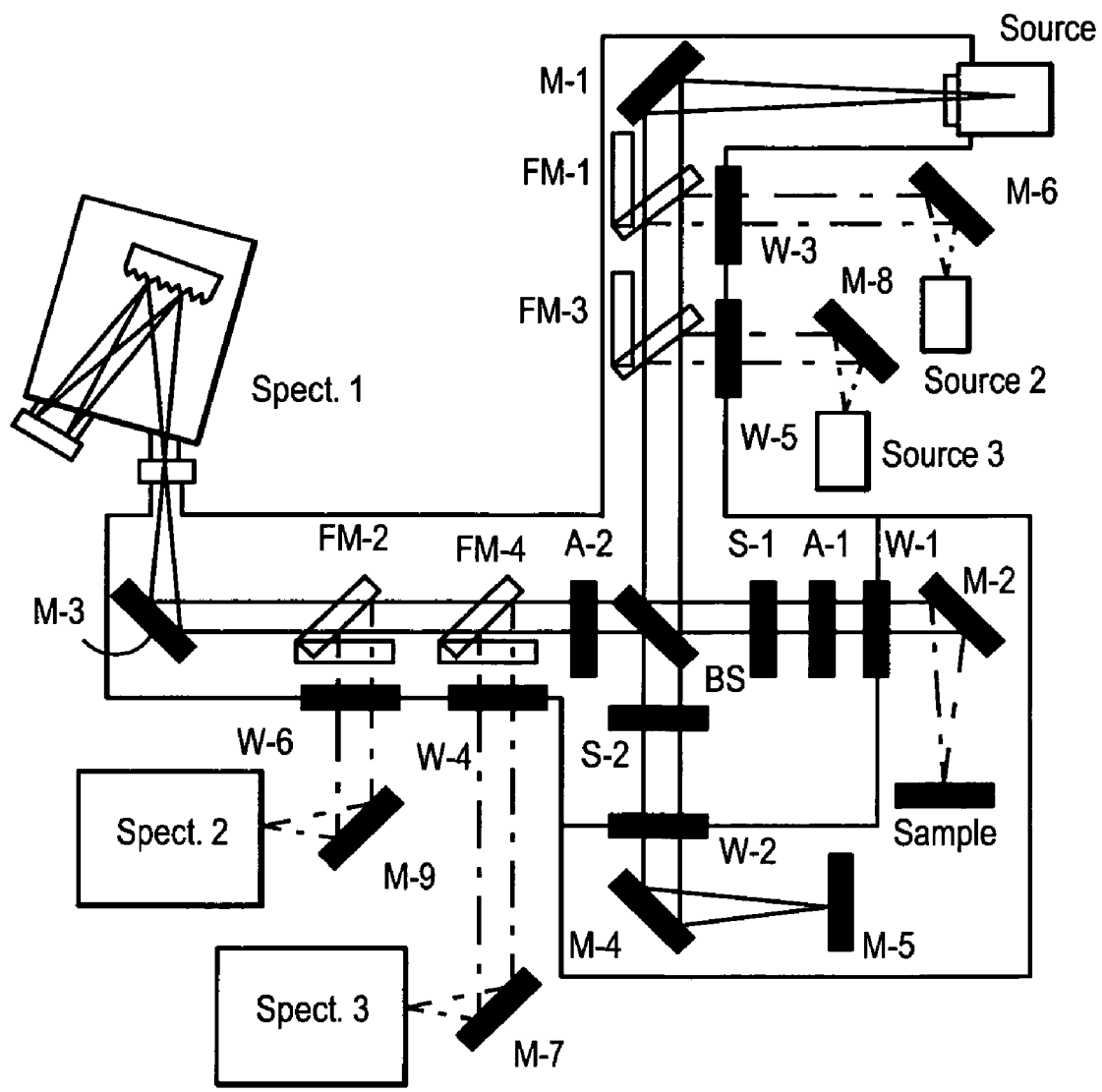
FIG. 4 illustrates an apparatus for collecting VUV-Vis reflectance data at multiple incident angles.

An example of a VUV metrology apparatus configured to collect multiple broadband data sets using different azimuthal incident angles is presented in FIG. 4. The instrument is separated into two environmentally controlled chambers, the instrument chamber and the sample chamber. The instrument chamber houses most of the system optics and is not opened to the atmosphere on a regular basis. The sample chamber houses the sample, the sample focusing optic M-2, the reference focusing optic M-4 and the reference plane mirror M-5. This chamber is opened regularly to facilitate changing samples. The instrument is configured to enable collection of sample and reference data sets. The reference data set can be used to correct for system and/or environmental changes which may occur between calibration and sample measurement times. The system may be configured with multiple sources and spectrometers/detectors that are selected using flip-in mirrors FM-1, FM-2, FM-3 and FM-4.

In operation the VUV data is first obtained by switching flip-in source mirrors FM-1 and FM-3 into the "out" position so as to allow light from the VUV source to be collected, collimated and redirected towards beam splitter element BS by focusing mirror M-1. Light striking the beam splitter is divided into two components, the sample beam and the reference beam, using a balanced Michelson interferometer arrangement. The sample beam is reflected from the beam splitter BS and travels through shutter S-1, aperture A-1 and VUV-transparent window W-1. Aperture A-1 is configured to restrict illumination of the sample to some azimuthal plane(s). Shutter S-2 is closed during this time.

Light entering the sample chamber is focused by focusing optic M-2 onto the sample. Light collected from the sample is collimated and redirected by mirror M-2 back through window W-1, aperture A-1 and beam splitter BS. Light passing through the beam splitter encounters aperture A-2, which is configured to selectively pass some fraction of the collected sample response. Light passing through aperture A-2 is redirected and focused onto the entrance slit of the VUV spectrometer by focusing mirror M-3. Flip-in detector mirrors FM-2 and FM-4 are switched to the "out" position during this time.

Following collection of the sample beam, the reference beam is measured by closing shutter S-1 and opening shutter S-2. Once the reference signal has been recorded, data from other spectral regions can be collected in a similar manner using the appropriate flip-in mirrors.

In totality, the use of VUV incident radiation, large polar incident angle or angles, and multiple azimuthal angles, can greatly enhance sensitivity to grating line shape parameters. An analysis using a series of simulations can be done for any given grating structure in order to determine which combination of incident polar angles, azimuthal angles, and wavelengths yields the most information for smallest computation cost.

For faster measurements, where a smaller amount of information may be desired (e.g. line height and average width only), it may be sufficient to use only the phi=90 incidence case and take advantage of the improved calculation speed over the corresponding classical phi=0 incidence case.

Another technique disclosed herein analyzes the multiple sets using different models. For instance, the phi=90 data might be analyzed using a simpler rectangular line shape model with a course parameter search to narrow down the average parameter values, and then a more thorough analysis done using another one of the spectrum (or all of the spectra together) with a more complicated model to further refine the line shape.

Review of the RCW Method for Conical Incidence

This review follows the notation of the Moharam and Gaylord references cited above. Many publications exist on the basic RCW method, some with notation differences and some with modifications to the formulations/derivation procedures such as that shown in the P. Lalanne and G. M. Morris reference cited above. It should be noted that the phi=90 case reduction described in this disclosure is can be applied to any of these formulations, and is not limited to just that of Moharam and Gaylord.

Note that unreduced eigen-problem matrix and vector indices run from −N to N, with the (−N, −N) matrix element at the top left corner, in order to be consistent with a symmetric diffraction problem with positive and negative orders. When creating a computer algorithm, the indices are labeled from 1 to 2N+1 (or 0 to 2N), depending on the programming language used. It will be recognized, this is a notation preference and has no effect on the outcome. The indices of the reduced matrices will run from 0 to N in either case.

Figure 1B:
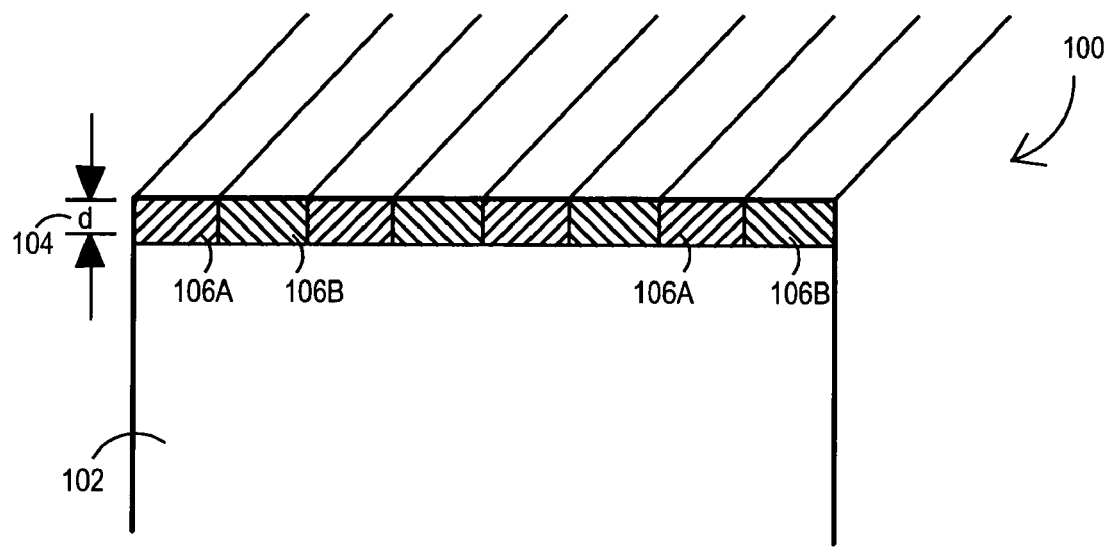

Following the Moharam and Gaylord references, the RCW method expands the fields in each region of FIG. 1 as a generalized Fourier series:

$$E_I = E_{inc} + \sum_i R_i \exp[-j(k_{xi}x + k_y y - k_{I,zi}z)] \quad \text{eq. 1}$$

$$E_{II} = \sum_i T_i \exp\{-j[k_{xi}x + k_y y + k_{II,zi}(z-d)]\} \quad \text{eq. 2}$$

in regions I and II, and $$E_g = \sum_i \begin{bmatrix} S_{xi}(z)x + S_{yi}(z)y + \\ S_{zi}(z)z \end{bmatrix} \exp[-j(k_{xi}x + k_y y)] \quad \text{eq. 3}$$

$$H_g = -j\left(\frac{\varepsilon_f}{\mu_f}\right)^{1/2} \sum_i \begin{bmatrix} U_{xi}(z)x + U_{yi}(z)y + \\ U_{zi}(z)z \end{bmatrix} \exp[-j(k_{xi}x + k_y y)] \quad \text{eq. 4}$$

in the grating region, where $$k_{xi} = k_0[n_I \sin\theta\cos\phi - i(\lambda_0/\Lambda)], \quad \text{eq. 5}$$

$$k_y = k_0 n_I \sin\theta \sin\phi, \quad \text{eq. 6}$$

$$k_{l,zi} = \begin{cases} [(k_0 n_l)^2 - k_{xi}^2 - k_y^2]^{1/2} & (k_{xi}^2 + k_y^2)^{1/2} < k_0 n_l \\ -j[k_{xi}^2 + k_y^2 - (k_0 n_l)^2]^{1/2} & (k_{xi}^2 + k_y^2)^{1/2} > k_0 n_l \end{cases} \quad \text{eq. 7}$$

$$l = I, II,$$

$k_0 = (2\pi/\lambda_0)$, $\lambda_0$ is the incident wavelength, and $\Lambda$ is the grating pitch. Note that for a 1D grating, $k_y$ is constant. In eqs. 3 and 4, $\epsilon_f$ is the permittivity of free space, and $\mu_f$ is the magnetic permeability of free space.

In equations 1 and 2, the $R_i$ and $T_i$ are the Fourier coefficients of the electric field in regions I and II, and correspond to the amplitudes of the reflected and transmitted diffraction orders. The diffracted orders can be propagating or evanescent. The corresponding magnetic fields can be obtained from Maxwell's relations $$\nabla \times E = -j\omega\mu_f H,$$

$$\nabla \times H = j\omega\epsilon_f \varepsilon(x) E, \quad \text{eq. 8}$$

where $\omega$ is the angular frequency, and $\mu$ is the magnetic permeability. Usually, one assumes $\mu = \mu_f$.

The complex permittivity in the grating region is also expanded as a Fourier series, which is $$\varepsilon(x) = \sum_h \varepsilon_h \exp\left(j\frac{2\pi h x}{\Lambda}\right), \quad \text{eq. 9}$$

$$\varepsilon_0 = n_{rd}^2 f + n_{gr}^2(1-f),$$

$$\varepsilon_h = (n_{rd}^2 - n_{gr}^2)\frac{\sin(\pi h f)}{\pi h}$$

for the binary grating structure of the first Moharam and Gaylord reference cited above and shown in FIG. 1. In eq. 9, $n_{rd}$ and $n_{gr}$ are the complex indices of refraction for the lines and spaces, respectively.

Eqs. 3, 4, 8, and 9 combine to give a set of coupled equations:

$$\begin{bmatrix} \frac{\partial S_y}{\partial(z')} \\ \frac{\partial S_x}{\partial(z')} \\ \frac{\partial U_y}{\partial(z')} \\ \frac{\partial U_x}{\partial(z')} \end{bmatrix} = \begin{bmatrix} 0 & 0 & K_y E^{-1} K_x & I - K_y E^{-1} K_y \\ 0 & 0 & K_x E^{-1} K_x - I & -K_x E^{-1} K_y \\ K_x K_y & E - K_y^2 & 0 & 0 \\ K_x^2 - E & -K_x K_y & 0 & 0 \end{bmatrix} \times \begin{bmatrix} S_y \\ S_x \\ U_y \\ U_x \end{bmatrix} \quad \text{eq. 10}$$

where $K_x$ is a diagonal matrix with elements $k_{xi}/k_0$, $K_y$ is a diagonal matrix with elements $k_y/k_0$, E is the permittivity matrix (not to be confused with the electric field), with $E_{i,j} = \epsilon_{(i-j)}$, and $z' = k_0 z$.

When a truncation order of N is used, eq. 10 is a system of $4(2N+1) \times 4(2N+1)$ coupled equations. The authors of the first Moharam and Gaylord reference cited above further reduce eq. 10 to two $2(2N+1) \times 2(2N+1)$ sets of equations:

$$\begin{bmatrix} \frac{\partial^2 S_y}{\partial(z')^2} \\ \frac{\partial^2 S_x}{\partial(z')^2} \end{bmatrix} = \begin{bmatrix} K_x^2 + DE & K_y[E^{-1}K_x E - K_x] \\ K_x[E^{-1}K_y E - K_y] & K_y^2 + BE \end{bmatrix} \begin{bmatrix} S_y \\ S_x \end{bmatrix}, \quad \text{eq. 11}$$

or $$\begin{bmatrix} \frac{\partial^2 U_y}{\partial(z')^2} \\ \frac{\partial^2 U_x}{\partial(z')^2} \end{bmatrix} = \begin{bmatrix} K_y^2 + EB & [K_x - E K_x E^{-1}] K_y \\ [K_y - E K_y E^{-1}] K_x & K_x^2 + ED \end{bmatrix} \begin{bmatrix} U_y \\ U_x \end{bmatrix}, \quad \text{eq. 12}$$

Where
$B = K_x E^{-1} K_x - I$ and $D = K_y E^{-1} K_y - I$.

These last equations are reduced still further into two $(2N+1) \times (2N+1)$ sets of equations:

$$[\partial^2 U_x / \partial(z')^2] = [K_y^2 + A][U_x] \quad \text{eq. 13}$$

and $$[\partial^2 S_x / \partial(z')^2] = [K_y^2 + BE][S_x], \quad \text{eq. 14}$$

where $A = K_x^2 - E$.

Later, Lalanne and Morris (cited above) were able to improve the convergence of the conical case by replacing the matrix E in the third row, second column of eq. 10 with the inverse of the inverse permittivity matrix, Einv, where $Einv_{i,j}=(1/\epsilon)_{i,j}$:

$$\begin{bmatrix} \frac{\partial S_y}{\partial(z')} \\ \frac{\partial S_x}{\partial(z')} \\ \frac{\partial U_y}{\partial(z')} \\ \frac{\partial U_x}{\partial(z')} \end{bmatrix} = \quad \text{eq. 15}$$

$$\begin{bmatrix} 0 & 0 & K_y E^{-1} K_x & I - K_y E^{-1} K_y \\ 0 & 0 & K_x E^{-1} K_x - I & -K_x E^{-1} K_y \\ K_x K_y & Einv^{-1} - K_y^2 & 0 & 0 \\ K_x^2 - E & -K_x K_y & 0 & 0 \end{bmatrix} \times \begin{bmatrix} S_y \\ S_x \\ U_y \\ U_x \end{bmatrix}$$

which lead to $$[\partial^2 U_x/\partial(z')^2]=[K_y^2+A][U_x], \quad \text{eq. 16}$$

and $$[\partial^2 S_x/\partial(z')^2]=[K_y^2+BEinv^{-1}][S_x] \quad \text{eq. 17}$$

in place of eqs. 13 and 14.

The new formulation eqs. 16 and 17 are advantageous and it may be noted that E and $Einv^{-1}$ are not the same matrices when they are truncated. The details can be found in references cited above from P. Lalanne and G. M. Morris; G. Granet and B. Guizal; and L. Li.

Equations 16 and 17 are solved by finding the eigenvalues and eigenvectors of the matrices $[K_y^2+A]$ and $[K_y^2+BEinv^{-1}]$, which leads to $$U_{xi} = \sum_{m=1}^{2N+1} w_{1,i,m} \left\{ \begin{array}{l} -c_{1,m}^+ \exp(-k_0 q_{1,m} z) + \\ c_{1,m}^- \exp[k_0 q_{1,m}(z-d)] \end{array} \right\}, \quad \text{eq. 18}$$

$$S_{xi}(z) = \sum_{m=1}^{2N+1} w_{2,i,m} \left\{ \begin{array}{l} c_{2,m}^+ \exp(-k_0 q_{2,m} z) + \\ c_{2,m}^- \exp[k_0 q_{2,m}(z-d)] \end{array} \right\}, \quad \text{eq. 19}$$

$$S_{yi}(z) = \sum_{m=1}^{2N+1} v_{11,i,m} \left\{ \begin{array}{l} c_{1,m}^+ \exp(-k_0 q_{1,m} z) + \\ c_{1,m}^- \exp[k_0 q_{1,m}(z-d)] \end{array} \right\} + \quad \text{eq. 20}$$

$$\sum_{m=1}^{2N+1} v_{1,2,i,m} \left\{ \begin{array}{l} c_{2,m}^+ \exp(-k_0 q_{2,m} z) + \\ c_{2,m}^- \exp[k_0 q_{2,m}(z-d)] \end{array} \right\},$$

$$U_{yi}(z) = \sum_{m=1}^{2N+1} v_{21,i,m} \left\{ \begin{array}{l} -c_{1,m}^+ \exp(-k_0 q_{1,m} z) + \\ c_{1,m}^- \exp[k_0 q_{1,m}(z-d)] \end{array} \right\} + \quad \text{eq. 21}$$

$$\sum_{m=1}^{2N+1} v_{22,i,m} \left\{ \begin{array}{l} -c_{2,m}^+ \exp(-k_0 q_{2,m} z) + \\ c_{2,m}^- \exp[k_0 q_{2,m}(z-d)] \end{array} \right\},$$

where $$V_{11} = A^{-1} W_1 Q_1, \quad \text{eq. 22}$$

$$V_{12} = (k_y/k_0) A^{-1} K_x W_2, \quad \text{eq. 23}$$

$$V_{21} = (k_y/k_0) B^{-1} K_x E^{-1} W_1, \quad \text{eq. 24}$$

$$V_{22} = B^{-1} W_2 Q_2, \quad \text{eq. 25}$$

$Q_1$ and $Q_2$ are diagonal matrices with elements $q_{1,m}$ and $q_{2,m}$, which are the square roots of the 2N+1 eigenvalues of the matrices $[K_y^2+A]$ and $[K_y^2+BEinv^{-1}]$, and $W_1$ and $W_2$ are the $(2N+1)\times(2N+1)$ matrices formed by the corresponding eigenvectors, with elements $w_{1,i,m}$ and $w_{2,i,m}$. Eqs. 16-25 constitute the eigen-problem portion of the RWC method given in the first the Moharam and Gaylord reference cited above. It is noted that there are other equivalent formulations of the same eigen-problem that will lead to the same final results.

The constants $c_{1,m}^+, c_{1,m}^-, c_{2,m}^+, c_{2,m}^-$ are determined by matching the tangential electric and magnetic field components at the two boundary regions of the grating. The first of the Moharam and Gaylord reference cited above uses a boundary formulation where the field components are rotated into the corresponding diffraction plane, $\phi_i$, for each diffracted order:

$$\sin\psi\delta_{i0}+R_{s,i}=\cos\phi_i S_{yi}(0)-\sin\phi_i S_{xi}(0), \quad \text{eq. 26}$$

$$j[\sin\psi n_I \cos\theta\delta_{i0}-(k_{I,zi}/k_0)R_{s,i}]=-[\cos\phi_i U_{xi}(0)+\sin\phi_i U_{yi}(0)], \quad \text{eq. 27}$$

$$\cos\psi\cos\theta\delta_{i0}-j[k_{I,zi}/(k_0 n_I^2)]R_{p,i}=\cos\phi_i S_{xi}(0)+\sin\phi_i S_{yi}(0) \quad \text{eq. 28}$$

$$-jn_I \cos\psi\delta_{i0}+R_{p,i}=-[\cos\phi_i U_{yi}(0)-\sin\phi_i U_{xi}(0)], \quad \text{eq. 29}$$

where $$\phi_i=\tan^{-1}(k_y/k_{xi}), \quad \text{eq. 30}$$

$$R_{s,i}=\cos\phi_i R_{yi}-\sin\phi_i R_{xi}, \quad \text{eq. 31}$$

$$R_{p,i}=(j/k_0)[\cos\phi_i(k_{I,zi}R_{xi}+k_{xi}R_{zi})+\sin\phi_i(k_y R_{zi}+k_{I,zi}R_{yi})], \quad \text{eq. 32}$$

at the z=0 boundary, and $$\cos\phi_i S_{yi}(d)-\sin\phi_i S_{xi}(d)=T_{s,i}, \quad \text{eq. 33}$$

$$-[\cos\phi_i U_{xi}(d)+\sin\phi_i U_{yi}(d)]=j(k_{I,zi}/k_0)T_{s,i}, \quad \text{eq. 34}$$

$$-[\cos\phi_i U_{yi}(d)-\sin\phi_i U_{xi}(d)]=T_{p,i}, \quad \text{eq. 35}$$

$$\cos\phi_i S_{xi}(d)+\sin\phi_i S_{yi}(d)=j(k_{I,zi}/k_0 n_I^2)T_{p,i}, \quad \text{eq. 36}$$

$$T_{s,i}=\cos\phi_i T_{yi}-\sin\phi_i T_{xi}, \quad \text{eq. 37}$$

$$T_{p,i}=(-j/k_0)[\cos\phi_i(k_{II,zi}T_{xi}-k_{xi}T_{zi})-\sin\phi_i(-k_{II,zi}T_{yi}+k_y T_{zi})] \quad \text{eq. 38}$$

at the z=d boundary. Note that there is one equation for each spatial harmonic retained in the Fourier expansions. $R_{s,i}$ and $R_{p,i}$ are the components of the reflected electric and magnetic field amplitudes normal to the diffraction plane, and $T_{s,i}$ and $T_{p,i}$ are the transmitted amplitudes.

In matrix form, eqs. 26-29 are $$\begin{bmatrix} \sin\psi\delta_{i0} \\ j\sin\psi n_I\cos\theta\delta_{i0} \\ -j\cos\psi n_I\delta_{i0} \\ \cos\psi\cos\theta\delta_{i0} \end{bmatrix} + \begin{bmatrix} I & 0 \\ -jY_I & 0 \\ 0 & I \\ 0 & -jZ_I \end{bmatrix} \begin{bmatrix} R_s \\ R_p \end{bmatrix} = \begin{bmatrix} V_{ss} & V_{sp} & V_{ss}X_1 & V_{sp}X_2 \\ W_{ss} & W_{sp} & -W_{ss}X_1 & -W_{sp}X_2 \\ W_{ps} & W_{pp} & -W_{ps}X_1 & -W_{pp}X_2 \\ V_{ps} & V_{pp} & V_{ps}X_1 & V_{pp}X_2 \end{bmatrix} \begin{bmatrix} c_1^+ \\ c_2^+ \\ c_1^- \\ c_2^- \end{bmatrix} \quad \text{eq. 39}$$

for the z=0 boundary and eqs. 33-36 are $$\begin{bmatrix} V_{ss}X_1 & V_{sp}X_2 & V_{ss} & V_{sp} \\ W_{ss}X_1 & W_{sp}X_2 & -W_{ss} & -W_{sp} \\ W_{ps}X_1 & W_{pp}X_2 & -W_{ps} & -W_{pp} \\ V_{ps}X_1 & V_{pp}X_2 & V_{ps} & V_{pp} \end{bmatrix} \begin{bmatrix} c_1^+ \\ c_2^+ \\ c_1^- \\ c_2^- \end{bmatrix} = \begin{bmatrix} I & 0 \\ jY_{II} & 0 \\ 0 & I \\ 0 & jZ_{II} \end{bmatrix} \begin{bmatrix} T_s \\ T_p \end{bmatrix} \quad \text{eq. 40}$$

for the z=d boundary, where $$V_{ss}=F_cV_{11} \quad W_{pp}=F_cV_{22}$$

$$W_{ss}=F_cW_1+F_sV_{21} \quad V_{pp}=F_cW_2+F_sV_{12}$$

$$V_{sp}=F_cV_{12}-F_sW_2 \quad W_{ps}=F_cV_{21}-F_sW_1$$

$$W_{sp}=F_sV_{22} \quad V_{ps}=F_sV_{11} \quad \text{eq. 41}$$

$Y_I$, $Y_{II}$, $Z_I$, and $Z_{II}$ are diagonal matrices with elements $(k_{I,zi}/k_0)$, $(k_{II,zi}/k_0)$, $(k_{I,zi}/k_0n_I^2)$, and $(k_{II,zi}/k_0n_{II}^2)$, respectively, $X_1$ and $X_2$ are diagonal matrices with elements $\exp(-k_{0q1,m}d)$ and $\exp(-k_{0q2,m}d)$, respectively, and $F_c$ and $F_s$ are diagonal matrices with elements $\cos\phi_i$ and $\sin\phi_i$, respectively.

Eqs. 39 and 40 are typically solved by eliminating $R_s$ and $R_p$ from eq. 39, $T_s$ and $T_p$ from eq. 40 and solving the resulting 4(2N+1) equations for the 4(2N+1) coefficients $c_{1,m}^+$, $c_{1,m}^-$, $c_{2,m}^+$, $c_{2,m}^-$ which can be substituted back into 39 and 40 to solve for the reflected and transmitted amplitudes.

Alternately, a procedure similar to the partial solution approach given in the second Moharam and Gaylord reference cited above can be used to determine reflected amplitudes only, giving a 2(2N+1)×2(2N+1) system of equations for the $c_{1,m}^+$ and $c_{2,m}^+$ coefficients:

$$j(Y_I)_{0,0}\sin\psi\delta_{i0} + j\sin\psi n_I\cos\theta\delta_{i0} = [jY_I f_T + f_B]\begin{bmatrix} c_1^+ \\ c_2^+ \end{bmatrix} \quad \text{eq. 42}$$

$$(Z_I)_{0,0}\cos\psi n_I\delta_{i0} + \cos\psi\cos\theta\delta_{i0} = [jZ_I g_T + g_B]\begin{bmatrix} c_1^+ \\ c_2^+ \end{bmatrix} \quad \text{eq. 43}$$

which are related to the reflected amplitudes:

$$R_s = f_T\begin{bmatrix} c_1^+ \\ c_2^+ \end{bmatrix} - \sin\psi\delta_{i0}, \quad \text{eq. 44}$$

$$R_p = g_T\begin{bmatrix} c_1^+ \\ c_2^+ \end{bmatrix} + j\cos\psi n_I\delta_{i0} \quad \text{eq. 45}$$

where $$\begin{bmatrix} f_T \\ f_B \\ g_T \\ g_B \end{bmatrix} = \begin{bmatrix} V_{ss} & V_{sp} \\ W_{ss} & W_{sp} \\ W_{ps} & W_{pp} \\ V_{ps} & V_{pp} \end{bmatrix} + \begin{bmatrix} V_{ss}X_1 & V_{sp}X_2 \\ -W_{ss}X_1 & -W_{sp}X_2 \\ -W_{ps}X_1 & -W_{pp}X_2 \\ V_{ps}X_1 & V_{pp}X_2 \end{bmatrix} \cdot a, \quad \text{eq. 46}$$

and the matrix a is defined as the top half of $$\begin{bmatrix} -V_{ss} & -V_{sp} & I & 0 \\ W_{ss} & W_{sp} & jY_{II} & 0 \\ W_{ps} & W_{pp} & 0 & I \\ -V_{ps} & V_{pp} & 0 & jZ_{II} \end{bmatrix}^{-1} \begin{bmatrix} V_{ss}X_1 & V_{sp}X_2 \\ W_{ss}X_1 & W_{sp}X_2 \\ W_{ps}X_1 & W_{pp}X_2 \\ V_{ps}X_1 & V_{pp}X_2 \end{bmatrix} \equiv \begin{bmatrix} a \\ b \end{bmatrix}. \quad \text{eq. 47}$$

Note that $(Y_I)_{0,0}$ and $(Z_I)_{0,0}$ refer to the center elements of the matrices $Y_I$, or $(k_{I,z0}/k_0)$, and $Z_I$, or $(k_{I,z0}/k_0n_I^2)$, respectively.

The boundary matching can be generalized to multiple layers using (for example) the enhanced transmittance matrix approach outlined in the second the Moharam and Gaylord reference cited above. Given an L layer stack, where L+1 refers to the substrate, start by setting $$\begin{bmatrix} f_{L+1,T} \\ f_{L+1,B} \\ g_{L+1,T} \\ g_{L+1,B} \end{bmatrix} = \begin{bmatrix} I & 0 \\ jY_{II} & 0 \\ 0 & I \\ 0 & jZ_{II} \end{bmatrix}. \quad \text{eq. 48}$$

The matrices for $a_L$ and $b_L$ are constructed for layer L, $$\begin{bmatrix} -V_{ss,L} & -V_{sp,L} & f_{L+1,T} \\ W_{ss,L} & W_{sp,L} & f_{L+1,B} \\ W_{ps,L} & W_{pp,L} & g_{L+1,T} \\ -V_{ps,L} & V_{pp,L} & g_{L+1,B} \end{bmatrix}^{-1} \begin{bmatrix} V_{ss,L}X_{1,L} & V_{sp,L}X_{2,L} \\ W_{ss,L}X_{1,L} & W_{sp,L}X_{2,L} \\ W_{ps,L}X_{1,L} & W_{pp,L}X_{2,L} \\ V_{ps,L}X_{1,L} & V_{pp,L}X_{2,L} \end{bmatrix} \equiv \begin{bmatrix} a_L \\ b_L \end{bmatrix}, \quad \text{eq. 49}$$

where $W_L$ and $V_L$ come from the solution to the eigen-problem for layer L, $X_{1,L}=\exp(-k_{0q1,m,L}d_L)$, and $X_{2,L}=\exp(-k_{0q2,m,L}d_L)$, where $d_L$ is the thickness of layer L. $f_L$ and $g_L$ are then obtained from $$\begin{bmatrix} f_{L,T} \\ f_{L,B} \\ g_{L,T} \\ g_{L,B} \end{bmatrix} = \begin{bmatrix} V_{ss,L} & V_{sp,L} \\ W_{ss,L} & W_{sp,L} \\ W_{ps,L} & W_{pp,L} \\ V_{ps,L} & V_{pp,L} \end{bmatrix} + \begin{bmatrix} V_{ss,L}X_{1,L} & V_{sp,L}X_{2,L} \\ -W_{ss,L}X_{1,L} & -W_{sp,L}X_{2,L} \\ -W_{ps,L}X_{1,L} & -W_{pp,L}X_{2,L} \\ V_{ps,L}X_{1,L} & V_{pp,L}X_{2,L} \end{bmatrix} \cdot a_L. \quad \text{eq. 50}$$

$f_L$ and $g_L$ are fed back into eq. 49 along with the solution to the eigen-problem for layer L-1 to find $a_{L-1}$ and $b_{L-1}$, and so on until at the top layer $f_{1T}$, $f_{1B}$, $g_{1T}$, and $g_{1B}$ are obtained. These are substituted into eqs. 42-45 in place of $f_T$, $f_B$, $g_T$, and $g_B$ to solve for the coefficients $c_{1,m}^+$ and $c_{2,m}^+$ for the top layer, and finally for the reflection coefficients for the diffracted orders via eqs. 44 and 45.

Eqs. 42 and 43 reduce the boundary problem to a 2(2N+1)×2(2N+1) set of equations. For large truncation order, the boundary problem can still be dominated by the 4(2N+1)×4

(2N+1) matrix inversion in eq. 49, but efficient inversion techniques can be employed since only the top half of the matrix is used.

Therefore, for a given incident polar angle theta, the computational expense incurred by using nonzero azimuthal incidence phi is two $(2N+1)\times(2N+1)$ eigen-problems versus one $(2N+1)\times(2N+1)$ eigen-problem in the corresponding classical (same theta, phi=0) case, a $2(2N+1)\times2(2N+1)$ linear system of equations for the boundary problem (to solve for reflected amplitudes only) versus a $(2N+1)\times(2N+1)$ system of equations in the corresponding classical incidence case, and a $4(2N+1)\times4(2N+1)$ matrix inversion in the boundary problem versus a $2(2N+1)\times2(2N+1)$ matrix inversion in the corresponding classical mount. Since these operations are governed by order $n^3$ operations, the conical mount requires approximately 2 times the computing time as the corresponding classical mount case for the eigen-problem, and approximately 8 times the computing time for the boundary problem.

Details of the Reduction in RCW Computation Time for the phi=90 Conical Mount

For the purposes of this description, the symmetry properties of the Fourier series are assumed a priori, and not proved. The initial assumptions can be derived through symmetry arguments, or by experimentation with the conventional formulation given above. In particular, for the phi=90 mount and s polarized incident light (psi=90), $$E_{x,i}=E_{x,-i} \qquad \text{eq. 51}$$

$$E_{y,i}=-E_{y,-i} \qquad \text{eq. 52}$$

$$H_{x,i}=-H_{x,-i} \qquad \text{eq. 53}$$

$$H_{y,i}=H_{y,-i}, \qquad \text{eq. 54}$$

while for p polarized incident light (psi=0), $$E_{x,i}=-E_{x,-i} \qquad \text{eq. 55}$$

$$E_{y,i}=E_{y,-i} \qquad \text{eq. 56}$$

$$H_{x,i}=H_{x,-i} \qquad \text{eq. 57}$$

$$H_{y,i}=-H_{y,-i}. \qquad \text{eq. 58}$$

In equations 51-58, the subscript i refers to the expansion term, which in the incident region corresponds to the diffraction order.

These relationships are valid in all regions of the grating problem, and all of the Fourier expansions can be reduced accordingly. In addition to these relationships, there is a 180 degree phase difference between opposite odd orders, but this can be ignored when not considering interference between multiple gratings.

Also, for phi=90, eq. 5 becomes $$k_{xi}=-ik_0(\lambda_0/\Lambda) \qquad \text{eq. 59}$$

This gives $$k_{xi}=-k_{x-i} \qquad \text{eq. 60}$$

$$k_{lzi}=k_{lz-i} \qquad \text{eq. 61}$$

The relations 51-61 show that for the phi=90 incidence case:
i) The generalized Fourier expansions in eqs. 1-4 become regular Fourier expansions, and
ii) The Fourier expansions for the fields have either even or odd symmetry, depending on the particular field component.

This means that a complex Fourier series representation is not necessary, and the field components can be expressed as cosine series for even symmetry cases or sine series for odd symmetry cases—although the Fourier coefficients themselves will still in general be complex. In either case, the entire content of the 2N+1 terms of a truncated complex Fourier series is contained in the N+1 terms of a cosine or sine series, depending on the symmetry. The usefulness of this for the grating problem arises from the fact that the fields have this symmetry in every region. When re-expressed as cosine and sine series, all of the information about the grating problem is contained in roughly half the number of terms required for the traditional formulation. This leads to a reduction in computation time by a factor of approximately 8 compared with the usual phi=90 formulation.

Each incident polarization case will be treated separately. For s polarized light, incident at polar angle theta and the phi=90 conical plane, eqs. 51-54 give $$S_{x,i}=S_{x,-i} \qquad \text{eq. 62}$$

$$S_{y,i}=-S_{y,-i} \qquad \text{eq. 63}$$

$$U_{x,i}=-U_{x,-i} \qquad \text{eq. 64}$$

$$U_{y,i}=U_{y,-i}, \qquad \text{eq. 65}$$

in the grating region.

The reduced Eqs. 26-29 and eqs. 33-36 may be derived by substituting the symmetry relations for $R_i$ and $T_i$ into eqs. 1-4 (this requires determining further symmetry relations for $R_{z,i}$ and $T_{z,i}$), reducing the fields everywhere to the appropriate Fourier cosine or sine series, applying the boundary conditions to the tangential components of the fields at z=0 and z=d, and rotating the boundary equations into the diffraction plane. However, the notation is unnecessarily cumbersome, and it is easier to apply eqs. 62-65 directly to eqs. 26-29 and eqs. 33-36 and use $$R_{s,i}=R_{s,-i} \qquad \text{eq. 66}$$

$$R_{p,i}=-R_{p,-i} \qquad \text{eq. 67}$$

$$T_{s,i}=T_{s,-i} \qquad \text{eq. 68}$$

$$T_{p,i}=-T_{p,-i}, \qquad \text{eq. 69}$$

to derive the same thing. Eqs. 66-69 can again be verified using the conventional formulation with the phi=90 mount.

In addition, eq. 30 for phi=90 gives $$\cos \phi_i = -\cos \phi_{-i} \qquad \text{eq. 70}$$

and $$\sin \phi_i = \sin \phi_{-i}. \qquad \text{eq. 71}$$

Applying the symmetry relations, the i=0 terms in eqs. 26-29 and eqs. 33-36 remain the same, but the nonzero i terms can be combined by adding the i and −i terms of eqs. 26, 27, 33, and 34, and subtracting the −ith from the ith terms in eqs. 28, 29, 35, and 36.

For example, eq. 26 gives $$\sin \psi + R_{s,0} = -S_{x,0}(0) \qquad \text{eq. 72}$$

for i=0, and $$R_{s,i}+R_{s,-i}=\cos \phi_i S_{y,i}(0)+\cos \phi_{-i} S_{y,-i}(0)-\sin \phi_i S_{x,i}(0)-\sin \phi_{-i} S_{x,-i}(0),$$

$$2R_{s,i}=2 \cos \phi_i S_{y,i}(0)-2 \sin \phi_i S_{x,i}(0),$$

$$R_{s,i}=\cos \phi_i S_{y,i}(0)-\sin \phi_i S_{x,i}(0), \qquad \text{eq. 73}$$

which is the same as eq. 26, except that i>0.

Similarly, eq. 28 gives $$\cos\psi \cos\theta - j[k_{I,z0}/(k_0 n_I^2)]R_{p,0} = S_{y,0}(0) \qquad \text{eq. 74}$$

for i=0, and $$-j[k_{I,zi}/(k_0 n_I^2)]R_{p,i} + j[k_{I,z(-i)}/(k_0 n_I^2)]R_{p,-i} = \cos\phi_i S_{x,i}(0) - \cos\phi_{-i} S_{x,-i}(0) + \sin\phi_i S_{y,i}(0) - \sin\phi_{-i} S_{y,-i}(0)$$

$$-2j[k_{I,zi}/(k_0 n_I^2)]R_{p,i} = 2\cos\phi_i S_{x,i}(0) + 2\sin\phi_i S_{y,i}(0),$$

$$-j[k_{I,zi}/(k_0 n_I^2)]R_{p,i} = \cos\phi_i S_{x,i}(0) + \sin\phi_i S_{y,i}(0), \qquad \text{eq. 75}$$

which is eq. 28, but with i>0.

The other boundary equations can be similarly reduced, and the form of the boundary problem is the same as the conventional one, except that only the i=0 and i>0 terms occur in the matrix equations. This reduces the matrix boundary problem (eqs. 39 and 40) to 4(N+1)×4(N+1) systems of equations, but leaves the form the same as in eqs. 26-41, as long as it is possible to also reduce the solution in the grating region to determining 4(N+1) coefficients $c_{1,m}^+$, $c_{1,m}^-$, $c_{2,m}^+$, $c_{2,m}^-$ instead of 4(2N+1) coefficients. This is shown to be the case below. Therefore, except for modifying the matrices to consist of N+1 harmonic terms (and therefore N+1 diffraction orders), the boundary problem is the same as previously defined. Now, $R_{si}$, $R_{pi}$, $T_{si}$, and $T_{pi}$ are the amplitudes of both the +i and -i diffracted orders.

To reduce the eigen-system, apply eqs. 60 and 62-65 directly to equations 15-17, reducing the total number of unknowns from 4(2N+1) to 4(N+1). The eigen-problems specified by eqs. 16 and 17 are each reduced from size (2N+1)×(2N+1) to size (N+1)×(N+1), for a total reduction of a factor of approximately 8 over the previous conical descriptions, and a factor of 4 over the corresponding classical mount eigen-problem.

Aside from reducing eqs. 16 and 17, reduced matrices for eqs. 22-25 will also need to be found. This will reduce the solution in the grating region to the determination of 4(N+1) coefficients instead of 4(2N+1).

Note that the symmetry of the lamellar grating also implies that the elements of the permittivity matrix satisfy $$E_{i,j} = E_{-i,-j}. \qquad \text{eq. 76}$$

The i th row of equation 16 can be written as $$\frac{\partial^2 U_{xi}}{\partial (z')^2} = \frac{k_y^2}{k_0^2} U_{xi} + \frac{k_{xi}^2}{k_0^2} U_{xi} - \sum_{m=-\infty}^{\infty} E_{i,m} U_{xm}. \qquad \text{eq. 77}$$

Due to eq. 64, eq. 16 obeys the following symmetry condition:

$$\frac{\partial^2 U_{xi}}{\partial (z')^2} = -\frac{\partial^2 U_{x-i}}{\partial (z')^2}. \qquad \text{eq. 78}$$

Subtracting the -i th row from the i th row gives $$\frac{\partial^2 U_{x0}}{\partial (z')^2} = \frac{k_y^2}{k_0^2} U_{x0} - \sum_{m=-\infty}^{\infty} E_{0,m} U_{xm} \qquad \text{eq. 79}$$

$$\frac{\partial^2 U_{x0}}{\partial (z')^2} = \frac{k_y^2}{k_0^2} U_{x0} - E_{0,0} U_{x0} - \sum_{m=-\infty}^{-1} E_{0,m} U_{xm} - \sum_{m=1}^{\infty} E_{0,m} U_{xm}$$

$$= \frac{k_y^2}{k_0^2} U_{x0} - E_{0,0} U_{x0} + \sum_{m=1}^{\infty} E_{0,-m} U_{xm} - \sum_{m=1}^{\infty} E_{0,m} U_{xm},$$

so $$\frac{\partial^2 U_{x0}}{\partial (z')^2} = \frac{k_y^2}{k_0^2} U_{x0} - \left\{ E_{0,0} U_{x0} + \sum_{m=1}^{\infty} (E_{0,m} - E_{0,-m}) U_{xm} \right\}$$

for $i = 0$, and $$2\frac{\partial^2 U_{xi}}{\partial (z')^2} = 2\frac{k_y^2}{k_0^2} U_{xi} + 2\frac{k_{xi}^2}{k_0^2} U_{xi} - \sum_{m=-\infty}^{\infty} E_{i,m} U_{xm} + \sum_{m=-\infty}^{\infty} E_{-i,m} U_{xm}$$

$$= 2\frac{k_y^2}{k_0^2} U_{xi} + 2\frac{k_{xi}^2}{k_0^2} U_{xi} - E_{i,0} U_{x0} - \sum_{m=-\infty}^{-1} E_{i,m} U_{xm} -$$

$$\sum_{m=1}^{\infty} E_{i,m} U_{xm} + E_{-i,0} U_{x0} + \sum_{m=-\infty}^{-1} E_{-i,m} U_{xm} + \sum_{m=1}^{\infty} E_{-i,m} U_{xm}$$

$$= 2\frac{k_y^2}{k_0^2} U_{xi} + 2\frac{k_{xi}^2}{k_0^2} U_{xi} - E_{i,0} U_{x0} + \sum_{m=1}^{\infty} E_{i,-m} U_{xm} -$$

$$\sum_{m=1}^{\infty} E_{i,m} U_{xm} + E_{-i,0} U_{x0} - \sum_{m=1}^{\infty} E_{-i,-m} U_{xm} + \sum_{m=1}^{\infty} E_{-i,m} U_{xm}$$

$$= 2\frac{k_y^2}{k_0^2} U_{xi} + 2\frac{k_{xi}^2}{k_0^2} U_{xi} - E_{i,0} U_{x0} + \sum_{m=1}^{\infty} E_{i,-m} U_{xm} -$$

$$\sum_{m=1}^{\infty} E_{i,m} U_{xm} + E_{-i,0} U_{x0} - \sum_{m=1}^{\infty} E_{-i,-m} U_{xm} + \sum_{m=1}^{\infty} E_{-i,m} U_{xm}$$

$$= 2\frac{k_y^2}{k_0^2} U_{xi} + 2\frac{k_{xi}^2}{k_0^2} U_{xi} - (E_{i,0} - E_{-i,0}) U_{x0} -$$

$$\sum_{m=1}^{\infty} (E_{i,m} + E_{-i,-m} - E_{i,-m} - E_{-i,m}) U_{xm},$$

so $$\frac{\partial^2 U_{xi}}{\partial (z')^2} = \frac{k_y^2}{k_0^2} U_{xi} + \frac{k_{xi}^2}{k_0^2} U_{xi} - \left\{ \begin{array}{l} \frac{1}{2}(E_{i,0} - E_{-i,0}) U_{x0} + \\ \frac{1}{2} \sum_{m=1}^{\infty} \left( \begin{array}{l} E_{i,m} + E_{-i,-m} - \\ E_{-i,m} - E_{i,-m} \end{array} \right) U_{xm} \end{array} \right\} \qquad \text{eq. 80}$$

for i>0. Note that i now runs from 0 to ∞ instead of -∞ to ∞.

The first two terms in eq. 79 and 80 indicate that the matrices $K_y^2$ and $K_x^2$ in eq. 16 should simply be replaced by diagonal matrices consisting of the 0 and positive terms of the original matrices. In fact, this will turn out to be the case for $K_x$ and $K_y$ throughout, and the subscripts and superscripts on these matrices distinguishing reduced from unreduced will hereafter be omitted.

The terms $$E_{i,0} U_{x0} + \sum_{m=1}^{\infty} (E_{0,m} - E_{0,-m}) U_{xm} \qquad \text{eq. 81}$$

from eq. 79 and $$\frac{1}{2}(E_{i,0} - E_{-i,0})U_{x0} + \frac{1}{2}\sum_{m=1}^{\infty}\begin{pmatrix} E_{i,m} + E_{-i,-m} - \\ E_{-i,m} - E_{i,-m} \end{pmatrix}U_{xm} \quad \text{eq. 82}$$

from eq. 80 are the rows of the reduced matrix that replaces the matrix E in eq. 16:

$$E^s_{reduced} = \quad \text{eq. 83}$$

$$\begin{bmatrix} E_{0,0} & E_{0,1} - E_{0,-1} & E_{0,2} - E_{0,-2} & \cdots \\ \frac{1}{2}(E_{1,0} - E_{-1,0}) & \frac{1}{2}\begin{pmatrix} E_{1,1} + E_{-1,-1} - \\ E_{-1,1} - E_{1,-1} \end{pmatrix} & \frac{1}{2}\begin{pmatrix} E_{1,2} + E_{-1,-2} - \\ E_{-1,2} - E_{1,-2} \end{pmatrix} & \cdots \\ \frac{1}{2}(E_{2,0} - E_{-2,0}) & \frac{1}{2}\begin{pmatrix} E_{2,1} + E_{-2,-1} - \\ E_{-2,1} - E_{2,-1} \end{pmatrix} & \frac{1}{2}\begin{pmatrix} E_{2,2} + E_{-2,-2} - \\ E_{-2,2} - E_{1,-2} \end{pmatrix} & \cdots \\ \vdots & & & \ddots \end{bmatrix}$$

with $$A^s_{reduced} = K_x^2 - E^s_{reduced} \quad \text{eq. 84}$$

and $$[\partial^2 U_x / \partial(z')^2] = [K_y^2 + A^s_{reduced}][U_x], \quad \text{eq. 85}$$

where the subscript s refers to the incident polarization case. All of the vectors in eq. 85 are of size N+1, and the matrices are of size (N+1)×(N+1) for a given truncation order, N.

Many of the terms in eq. 83 can be reduced using eq. 76, but it is more useful to assume nothing about the elements of the matrices being reduced. This way, other matrices that may not necessarily obey eq. 76 can be reduced using the same formulas. Along these lines, more general reductions can be formulated, which can be applied to a variety of matrices or even the products of matrices that will be required to find the reduced matrices of eqs. 22-25.

Disregarding the simpler diagonal matrices $K_y$ and $K_x$, the unreduced equations have the general form $$l[P_i] = \sum_{m=-\infty}^{\infty} \varepsilon_{i,m} Q_m \quad \text{eq. 86}$$

Where l is a linear operator, such as $$\frac{\partial}{\partial(z')} \text{ or } \frac{\partial^2}{\partial(z')^2},$$

and the elements of the vectors P and Q are spatial harmonic coefficients of the Fourier expansions for the corresponding fields. The goal is to find a reduced matrix for $\epsilon$ through application of symmetry relations to the vectors P and Q. Without making any assumptions about the elements of the matrix $\epsilon$, there are in general four types of reductions:
1) Both P and Q are even and the corresponding Fourier series can be reduced to cosine series,
2) Both P and Q are odd and the corresponding Fourier expressions can be reduced to sine series,
3) P is even and Q is odd,
4) P is odd and Q is even.

Note that if P has even or odd symmetry, then $$\frac{\partial P}{\partial(z')} \text{ and } \frac{\partial^2 P}{\partial(z')^2}$$

are also even or odd, respectively.

The reduction leading to eqs. 81 and 82 belongs to category 2. The same argument can be applied to eq. 86 to give $$l[P_0] = \varepsilon_{0,0} Q_0 + \sum_{m=1}^{\infty}(\varepsilon_{0,m} - \varepsilon_{0,-m})Q_m, \quad \text{eq. 87}$$

$i = 0,$ and $$l[P_i] = \frac{1}{2}(\varepsilon_{i,0} - \varepsilon_{-i,0})Q_0 + \frac{1}{2}\sum_{m=1}^{\infty}\begin{pmatrix} \varepsilon_{i,m} + \varepsilon_{-i,-m} - \\ \varepsilon_{-i,m} - \varepsilon_{i,-m} \end{pmatrix}Q_m, \quad \text{eq. 88}$$

$i > 0,$ for any matrix $\epsilon$ and field harmonics P and Q having odd symmetry.

The other 3 cases are developed below.

For case 1, both P and Q have even symmetry. Therefore the i and −i rows can be added together:

$$l[P_0] = \sum_{m=-\infty}^{\infty} \varepsilon_{0,m} Q_m \quad \text{eq. 89}$$

$$= \varepsilon_{0,0} Q_0 + \sum_{m=-\infty}^{-1} \varepsilon_{0,m} Q_m + \sum_{m=1}^{\infty} \varepsilon_{0,m} Q_m$$

$$= \varepsilon_{0,0m} Q_0 + \sum_{m=1}^{\infty} \varepsilon_{0,-m} Q_m + \sum_{m=1}^{\infty} \varepsilon_{0,m} Q_m$$

$$l[P_0] = \varepsilon_{0,0} Q_0 + \sum_{m=1}^{\infty}(\varepsilon_{0,m} + \varepsilon_{0,-m})Q_m, \quad i = 0,$$

and $$l[P_i] + l[P_{-i}] = \sum_{m=-\infty}^{\infty} \varepsilon_{i,m} Q_m + \sum_{m=-\infty}^{\infty} \varepsilon_{-i,m} Q_m \quad \text{eq. 90}$$

$$= \varepsilon_{i,0} Q_0 + \varepsilon_{-i,0} Q_0 + \sum_{m=-\infty}^{-1} \varepsilon_{i,m} Q_m +$$

$$\sum_{m=1}^{\infty} \varepsilon_{i,m} Q_m + \sum_{m=-\infty}^{-1} \varepsilon_{-i,m} Q_m + \sum_{m=1}^{\infty} \varepsilon_{-i,m} Q_m$$

$$= (\varepsilon_{i,0} + \varepsilon_{-i,0})Q_0 + \sum_{m=1}^{\infty} \varepsilon_{i,-m} Q_m + \sum_{m=1}^{\infty} \varepsilon_{i,m} Q_m +$$

$$\sum_{m=1}^{\infty} \varepsilon_{-i,-m} Q_m + \sum_{m=1}^{\infty} \varepsilon_{-i,m} Q_m$$

$$= (\varepsilon_{i,0} + \varepsilon_{-i,0})Q_0 +$$

$$\sum_{m=1}^{\infty}(\varepsilon_{i,m} + \varepsilon_{i,-m} + \varepsilon_{-i,m} + \varepsilon_{-i,-m})Q_m$$

$$= 2l[P_i],$$

so $$l[P_i] = \frac{1}{2}(\varepsilon_{i,0} + \varepsilon_{-i,0})Q_0 + \frac{1}{2}\sum_{m=1}^{\infty}\begin{pmatrix} \varepsilon_{i,m} + \varepsilon_{i,-m} + \\ \varepsilon_{-i,m} + \varepsilon_{-i,-m} \end{pmatrix}Q_m,$$

$i > 0.$

Eqs. 89 and 90 define a reduced matrix $$\varepsilon_{reduced} = \begin{bmatrix} \varepsilon_{0,0} & \varepsilon_{0,1}+\varepsilon_{0,-1} & \varepsilon_{0,2}+\varepsilon_{0,-2} & \cdots \\ \frac{1}{2}(\varepsilon_{1,0}+\varepsilon_{-1,0}) & \frac{1}{2}\begin{pmatrix}\varepsilon_{1,1}+\varepsilon_{-1,-1}+\\ \varepsilon_{1,-1}+\varepsilon_{-1,1}\end{pmatrix} & \frac{1}{2}\begin{pmatrix}\varepsilon_{1,2}+\varepsilon_{-1,-2}+\\ \varepsilon_{1,-2}+\varepsilon_{-1,2}\end{pmatrix} & \cdots \\ \frac{1}{2}(\varepsilon_{2,0}+\varepsilon_{-2,0}) & \frac{1}{2}\begin{pmatrix}\varepsilon_{2,1}+\varepsilon_{-2,-1}+\\ \varepsilon_{2,-1}+\varepsilon_{-2,1}\end{pmatrix} & \frac{1}{2}\begin{pmatrix}\varepsilon_{2,2}+\varepsilon_{-2,-2}+\\ \varepsilon_{2,-2}+\varepsilon_{-1,2}\end{pmatrix} & \cdots \\ \vdots & & & \ddots \end{bmatrix} \qquad \text{eq. 91}$$

For case 3, the i and −i rows are again added:

$$l[P_0] = \sum_{m=-\infty}^{\infty} \varepsilon_{0,m} Q_m \qquad \text{eq. 92}$$

$$= \varepsilon_{0,0} Q_0 + \sum_{m=-\infty}^{-1} \varepsilon_{0,m} Q_m + \sum_{m=1}^{\infty} \varepsilon_{0,m} Q_m$$

$$= \varepsilon_{0,0} Q_0 - \sum_{m=1}^{\infty} \varepsilon_{0,-m} Q_m + \sum_{m=1}^{\infty} \varepsilon_{0,m} Q_m,$$

$$l[P_0] = \varepsilon_{0,0} Q_0 + \sum_{m=1}^{\infty} (\varepsilon_{0,m} - \varepsilon_{0,-m}) Q_m, \quad i = 0,$$

and $$l[P_i] + l[P_{-i}] = \sum_{m=-\infty}^{\infty} \varepsilon_{i,m} Q_m + \sum_{m=-\infty}^{\infty} \varepsilon_{-i,m} Q_m$$

$$= \varepsilon_{i,0} Q_0 + \varepsilon_{-i,0} Q_0 + \sum_{m=-\infty}^{-1} \varepsilon_{i,m} Q_m +$$

$$\sum_{m=1}^{\infty} \varepsilon_{i,m} Q_m + \sum_{m=-\infty}^{-1} \varepsilon_{-i,m} Q_m +$$

$$\sum_{m=1}^{\infty} \varepsilon_{-i,m} Q_m$$

$$= (\varepsilon_{i,0} + \varepsilon_{-i,0}) Q_0 - \sum_{m=1}^{\infty} \varepsilon_{i,-m} Q_m +$$

$$\sum_{m=1}^{\infty} \varepsilon_{i,m} Q_m - \sum_{m=1}^{\infty} \varepsilon_{-i,-m} Q_m +$$

$$\sum_{m=1}^{\infty} \varepsilon_{-i,m} Q_m$$

$$= (\varepsilon_{i,0} + \varepsilon_{-i,0}) Q_0 +$$

$$\sum_{m=1}^{\infty} (\varepsilon_{i,m} + \varepsilon_{-i,m} - \varepsilon_{i,-m} - \varepsilon_{-i,-m}) Q_m$$

$$= 2l[P_i],$$

giving $$l[P_i] = \frac{1}{2}(\varepsilon_{i,0} + \varepsilon_{-i,0}) Q_0 + \qquad \text{eq. 93}$$

$$\frac{1}{2} \sum_{m=1}^{\infty} \begin{pmatrix} \varepsilon_{i,m} + \varepsilon_{-i,m} - \\ \varepsilon_{i,-m} - \varepsilon_{-i,-m} \end{pmatrix} Q_m, \quad i > 0.$$

For case 4, subtract the −i th row from the i th row:

$$l[P_0] = \sum_{m=-\infty}^{\infty} \varepsilon_{0,m} Q_m = \varepsilon_{0,0} Q_0 + \sum_{m=-\infty}^{-1} \varepsilon_{0,m} Q_m + \sum_{m=1}^{\infty} \varepsilon_{0,m} Q_m \qquad \text{eq. 94}$$

$$= \varepsilon_{0,0} Q_0 + \sum_{m=1}^{\infty} \varepsilon_{0,-m} Q_m + \sum_{m=1}^{\infty} \varepsilon_{0,m} Q_m,$$

$$l[P_0] = \varepsilon_{0,0} Q_0 + \sum_{m=1}^{\infty} (\varepsilon_{0,m} + \varepsilon_{0,-m} Q_m), \quad i = 0,$$

and $$l[P_i] - l[P_{-i}] = \sum_{m=-\infty}^{\infty} \varepsilon_{i,m} Q_m - \sum_{m=-\infty}^{\infty} \varepsilon_{-i,m} Q_m$$

$$= \varepsilon_{i,0} Q_0 - \varepsilon_{-i,0} Q_0 + \sum_{m=-\infty}^{-1} \varepsilon_{i,m} Q_m +$$

$$\sum_{m=1}^{\infty} \varepsilon_{i,m} Q_m - \sum_{m=-\infty}^{-1} \varepsilon_{-i,m} Q_m - \sum_{m=1}^{\infty} \varepsilon_{-i,m} Q_m$$

$$= (\varepsilon_{i,0} - \varepsilon_{-i,0}) Q_0 + \sum_{m=1}^{\infty} \varepsilon_{i,-m} Q_m +$$

$$\sum_{m=1}^{\infty} \varepsilon_{i,m} Q_m - \sum_{m=1}^{\infty} \varepsilon_{-i,-m} Q_m - \sum_{m=1}^{\infty} \varepsilon_{-i,m} Q_m$$

$$= (\varepsilon_{i,0} - \varepsilon_{-i,0}) Q_0 + \sum_{m=1}^{\infty} \begin{pmatrix} \varepsilon_{i,m} - \varepsilon_{i,-m} - \\ \varepsilon_{-i,m} - \varepsilon_{-i,-m} \end{pmatrix} Q_m$$

$$= 2l[P_i]$$

giving $$l[P_i] = \frac{1}{2}(\varepsilon_{i,0} - \varepsilon_{-i,0}) Q_0 + \qquad \text{eq. 95}$$

$$\frac{1}{2} \sum_{m=1}^{\infty} \begin{pmatrix} \varepsilon_{i,m} + \varepsilon_{i,-m} - \\ \varepsilon_{-i,m} - \varepsilon_{-i,-m} \end{pmatrix} Q_m, \quad i > 0.$$

Application of case 2 with $\epsilon=E$ leads directly to eqs. 81 and 82 for $E_{reduced}$ and leads to the reduced eigenproblem of eqs. 84 and 85. To reduce eq. 17, case 1 can be applied directly to the product $BEinv^{-1}$, giving $$\frac{\partial^2 S_{x0}}{\partial (z')^2} = \left(\frac{k_y^2}{k_0}\right) S_{x0} + (BEinv^{-1})_{0,0} S_{x0} + \qquad \text{eq. 96}$$

$$\sum_{m=1}^{\infty} [(BEinv^{-1})_{0,m} + (BEinv^{-1})_{0,-m}] S_{xm}$$

$$\frac{\partial^2 S_{xi}}{\partial (z')^2} = \left(\frac{k_y^2}{k_0}\right) S_{x,i} + \frac{1}{2}[(BEinv^{-1})_{i,0} + (BEinv^{-1})_{-i,0}] S_{x0} + \qquad \text{eq. 97}$$

$$\frac{1}{2}\begin{bmatrix}(BEinv^{-1})_{i,m} + (BEinv^{-1})_{i,-m} + \\ (BEinv^{-1})_{-i,m} + (BEinv^{-1})_{-i,-m}\end{bmatrix} S_{xm}.$$

This involves $(2N+1)\times(2N+1)$ matrix multiplications to find the elements of $BE_{inv}^{-1}$. A slightly more efficient way to construct the reduced eigen-problem is to reduce the components of the product first, and multiply the reduced $(N+1)\times(N+1)$ matrices together to form $B_{reduced}(Einv^{-1})_{reduced}$.

To do this one can go back to eq. 15 and apply the appropriate reductions to the third column of the second row and second column of the third row for B and $Einv^{-1}$, respectively.

For B, explicitly reduce the product $K_x E^{-1} K_x$:

$$\frac{\partial S_{xi}}{\partial (z')} = \ldots + \frac{k_{xi}}{k_0} \sum_{m=-\infty}^{\infty} (E^{-1})_{i,m} \frac{k_{xm}}{k_0} U_{ym}, \quad \text{eq. 98}$$

where the dots replace other terms in eq. 15 that are not relevant for the purpose of finding the reduced matrix.

Adding the i th and −i th rows:

$$\frac{\partial S_{x0}}{\partial (z')} = \ldots + 0, \quad i = 0, \quad \text{eq. 99}$$

since $k_{x0} = 0$, and $$2\frac{\partial S_{xi}}{\partial (z')} = \ldots + \frac{k_{xi}}{k_0} \sum_{m=-\infty}^{\infty} (E^{-1})_{i,m} \frac{k_{xm}}{k_0} U_{ym} +$$

$$\frac{k_{x-i}}{k_0} \sum_{m=-\infty}^{\infty} (E^{-1})_{-i,m} \frac{k_{xm}}{k_0} U_{ym}$$

$$= \ldots + \frac{k_{xi}}{k_0} \left[ \sum_{m=-\infty}^{-1} (E^{-1})_{i,m} \frac{k_{xm}}{k_0} U_{ym} + \sum_{m=1}^{\infty} (E^{-1})_{i,m} \frac{k_{xm}}{k_0} U_{ym} \right] +$$

$$\frac{k_{x-i}}{k_0} \left[ \sum_{m=-\infty}^{-1} (E^{-1})_{-i,m} \frac{k_{xm}}{k_0} U_{ym} + \sum_{m=1}^{\infty} (E^{-1})_{-i,m} \frac{k_{xm}}{k_0} U_{ym} \right]$$

$$= \ldots + \frac{k_{xi}}{k_0} \left[ \sum_{m=1}^{\infty} (E^{-1})_{i,-m} \frac{k_{x-m}}{k_0} U_{ym} + \sum_{m=1}^{\infty} (E^{-1})_{i,m} \frac{k_{xm}}{k_0} U_{ym} \right] +$$

$$\frac{k_{x-i}}{k_0} \left[ \sum_{m=1}^{\infty} (E^{-1})_{-i,-m} \frac{k_{x-m}}{k_0} U_{ym} + \sum_{m=1}^{\infty} (E^{-1})_{-i,m} \frac{k_{xm}}{k_0} U_{ym} \right]$$

$$= \ldots + \frac{k_{xi}}{k_0} \left[ -\sum_{m=1}^{\infty} (E^{-1})_{i,-m} \frac{k_{xm}}{k_0} U_{ym} + \sum_{m=1}^{\infty} (E^{-1})_{i,m} \frac{k_{xm}}{k_0} U_{ym} \right] -$$

$$\frac{k_{xi}}{k_0} \left[ -\sum_{m=1}^{\infty} (E^{-1})_{-i,-m} \frac{k_{xm}}{k_0} U_{ym} + \sum_{m=1}^{\infty} (E^{-1})_{-i,m} \frac{k_{xm}}{k_0} U_{ym} \right]$$

$$= \ldots + \frac{k_{xi}}{k_0} \left[ -\sum_{m=1}^{\infty} (E^{-1})_{i,-m} \frac{k_{xm}}{k_0} U_{ym} + \sum_{m=1}^{\infty} (E^{-1})_{i,m} \frac{k_{xm}}{k_0} U_{ym} - \sum_{m=1}^{\infty} (E^{-1})_{-i,m} \frac{k_{xm}}{k_0} U_{ym} \right]$$

$$= \ldots + \frac{k_{xi}}{k_0} \sum_{m=1}^{\infty} \left[ \frac{(E^{-1})_{i,m} + (E^{-1})_{-i,-m} -}{(E^{-1})_{i,-m} - (E^{-1})_{-i,m}} \right] \frac{k_{xm}}{k_0} U_{ym}$$

$$= \ldots + \frac{k_{xi}}{k_0} \sum_{m=1}^{\infty} [2(E^{-1})_{i,m} - 2(E^{-1})_{i,-m}] \frac{k_{xm}}{k_0} U_{ym},$$

giving $$2\frac{\partial S_{xi}}{\partial (z')} = \ldots + \frac{k_{xi}}{k_0} \sum_{m=1}^{\infty} [(E^{-1})_{i,m} - (E^{-1})_{i,-m}] \frac{k_{xm}}{k_0} U_{ym}, \quad \text{eq. 100}$$

$i > 0$, or $$(K_x E^{-1} K_x)^s_{reduced} = \quad \text{eq. 101}$$

$$\begin{bmatrix} 0 & 0 & 0 & \cdots \\ 0 & \frac{k_{x1}}{k_0}\left[\frac{(E^{-1})_{1,1} -}{(E^{-1})_{1,-1}}\right]\frac{k_{x1}}{k_0} & \frac{k_{x1}}{k_0}\left[\frac{(E^{-1})_{1,2} -}{(E^{-1})_{1,-2}}\right]\frac{k_{x2}}{k_0} & \cdots \\ 0 & \frac{k_{x2}}{k_0}\left[\frac{(E^{-1})_{2,1} -}{(E^{-1})_{2,-1}}\right]\frac{k_{x1}}{k_0} & \frac{k_{x2}}{k_0}\left[\frac{(E^{-1})_{2,2} -}{(E^{-1})_{2,-2}}\right]\frac{k_{x2}}{k_0} & \cdots \\ \vdots & & & \ddots \end{bmatrix}$$

in explicit form. Then $$B_{reduced}^s = (K_x E^{-1} K_x)_{reduced}^s - I \quad \text{eq. 102}$$

For $Einv^{-1}$, use $$\frac{\partial U_{yi}}{\partial z'} = \ldots + \sum_{m=-\infty}^{\infty} (Einv^{-1})_{im} S_{xm} \quad \text{eq. 103}$$

to which case 1 may be directly applied:

$$\frac{\partial U_{y0}}{\partial z'} = \ldots + (Einv^{-1})_{0,0} S_{x,0} + \sum_{m=1}^{\infty} 2(Einv^{-1})_{0,m} S_{xm}, \quad \text{eq. 104}$$

$i = 0$, $$\frac{\partial U_{yi}}{\partial z'} = \ldots + (Einv^{-1})_{i,0} S_{x,0} + \sum_{m=1}^{\infty} \left[ \frac{(Einv^{-1})_{i,m} +}{(Einv^{-1})_{i,-m}} \right] S_{xm}, \quad \text{eq. 105}$$

$i > 0$, which implies $$(Einv^{-1})_{reduced}^S = \begin{bmatrix} (Einv^{-1})_{0,0} & 2(Einv^{-1})_{0,1} & 2(Einv^{-1})_{0,2} & \cdots \\ (Einv^{-1})_{1,0} & \begin{matrix}(Einv^{-1})_{1,1} + \\ (Einv^{-1})_{1,-1}\end{matrix} & \begin{matrix}(Einv^{-1})_{1,2} + \\ (Einv^{-1})_{1,-2}\end{matrix} & \cdots \\ (Einv^{-1})_{2,0} & \begin{matrix}(Einv^{-1})_{2,1} + \\ (Einv^{-1})_{2,-1}\end{matrix} & \begin{matrix}(Einv^{-1})_{2,2} + \\ (Einv^{-1})_{2,-2}\end{matrix} & \cdots \\ \vdots & & & \ddots \end{bmatrix} \quad \text{eq. 106}$$

where one makes use of the fact that $(Einv^{-1})_{i,m} = (Einv^{-1})_{-i,-m}$.

Eq. 17 becomes $$[\partial^2 S_x / \partial (z')^2] = [K_y^2 + B_{reduced}^s (Einv^{-1})_{reduced}^s][S_x] \quad \text{eq. 107}$$

In eqs. 85 and 107 the vectors $S_x$ and $U_x$ and diagonal matrices $K_y$ and $K_x$ are trivially reduced to consist of the zeroth and positive terms of the original vectors/matrices. When truncated with truncation order N, the size of the eigen-problems are (N+1)×(N+1) instead of (2N+1)×(2N+1), and require much less computation time to solve.

The solution to the reduced eigen-problems has the same form as eqs. 18-25, but with 4(N+1) coefficients to be determined instead of 4(2N+1). The correct reduced matrices to use in eqs. 22-25 should still be found, so that the reduced form of eq. 15 is satisfied. Here again one could have derived the entire reduced set of eqs. for eq. 15, but it is really only necessary to reduce a few specific terms in order to find $A^{-1}$, $B^{-1}$, $A^{-1}K_x$, and $B^{-1}K_xE^{-1}$ to use in eqs. 22-25.

Substituting eqs. 18-21 into the second row of eq. 15 gives $$W_2Q_2=(K_xE^{-1}K_x-I)V_{22} \qquad \text{eq. 108}$$

and $$(K_xE^{-1}K_x-I)V_{21}=K_xE^{-1}K_yW_1. \qquad \text{eq. 109}$$

Substituting eq. 25 into eq. 108 gives $$W_2Q_2=BV_{22}=BB^{-1}W_2Q_2, \qquad \text{eq. 110}$$

which implies that $B^{-1}$ in eq. 25 should be replaced by the inverse of the reduced matrix $B_{reduced}$ found earlier.

Eqs. 24 and 109 give $$BV_{21}=BB^{-1}\left(\frac{k_y}{k_0}\right)K_xE^{-1}W_1=K_xE^{-1}K_yW_1, \qquad \text{eq. 111}$$

Which again implies that $B^{-1} \to (B_{reduced})^{-1}$ in eq. 24, and $K_xE^{-1}$ is found by reducing $$\frac{\partial S_x}{\partial(z')}=\ldots-K_xE^{-1}K_yU_x. \qquad \text{eq. 112}$$

Since $S_x$ is even in x and $U_x$ is odd, the reduced matrix for $K_xE^{-1}$ can be found by applying case 3 with $\epsilon=K_xE^{-1}$:

$$\frac{\partial S_{x0}}{\partial(z')}=\ldots-\left\{\begin{array}{l}(K_xE^{-1})_{0,0}U_{x0}+\\ \sum_{m=1}^{\infty}[(K_xE^{-1})_{0,m}-(K_xE^{-1})_{0,-m}]U_{xm}\end{array}\right\} \qquad \text{eq. 113}$$

for $i = 0$, and $$\frac{\partial S_{xi}}{\partial(z')}=\ldots\left\{\begin{array}{l}\frac{1}{2}[(K_xE^{-1})_{i,0}+(K_xE^{-1})_{-i,0}]U_{x0}+\\ \frac{1}{2}\sum_{m=1}^{\infty}\begin{bmatrix}(K_xE^{-1})_{i,m}+\\(K_xE^{-1})_{-i,m}-\\(K_xE^{-1})_{i,-m}-\\(K_xE^{-1})_{-i,-m}\end{bmatrix}U_{xm}\end{array}\right\}, i>0. \qquad \text{eq. 114}$$

This gives $$(K_xE^{-1})_{reduced}^S= \qquad \text{eq. 115}$$

$$\begin{bmatrix} (K_xE^{-1})_{0,0} & (K_xE^{-1})_{0,1}-(K_xE^{-1})_{0,-1} & \cdots \\ \frac{1}{2}\begin{bmatrix}(K_xE^{-1})_{1,0}+\\(K_xE^{-1})_{-1,0}\end{bmatrix} & \frac{1}{2}\begin{bmatrix}(K_xE^{-1})_{1,1}+(K_xE^{-1})_{-1,1}-\\(K_xE^{-1})_{1,-1}-(K_xE^{-1})_{-1,-1}\end{bmatrix} & \cdots \\ \frac{1}{2}\begin{bmatrix}(K_xE^{-1})_{2,0}+\\(K_xE^{-1})_{-2,0}\end{bmatrix} & \frac{1}{2}\begin{bmatrix}(K_xE^{-1})_{2,1}+(K_xE^{-1})_{-2,1}-\\(K_xE^{-1})_{2,-1}-(K_xE^{-1})_{-2,-1}\end{bmatrix} & \cdots \\ \vdots & & \ddots \end{bmatrix}$$

Substituting eqs. 18-20, 22, and 23 into the fourth row of eq. 15 gives $$W_1Q_1=(K_x^2-E)V_{11}=AV_{11}=AA^{-1}W_1Q_1 \qquad \text{eq. 116}$$

and $$(K_x^2-E)V_{12}=AV_{12}=AA^{-1}K_xK_yW_2. \qquad \text{eq. 117}$$

Since A is replaced by $A_{reduced}$ in eqs. 116 and 117, $A^{-1}$ should be replaced by $(A_{reduced})^{-1}$ in both eqs. 22 and 23. $K_x$ is simply replaced by a diagonal matrix with the $(K_x)_{00}$, $(K_x)_{11}, \ldots, (K_x)_{NN}$ components of the original $K_x$ matrix, as always.

Therefore eqs. 22-25 are replaced by $$V_{11}=(A_{reduced}^s)^{-1}W_1Q_1, \qquad \text{eq. 118}$$

$$V_{12}=(k_y/k_0)(A_{reduced}^s)^{-1}K_xW_2, \qquad \text{eq. 119}$$

$$V_{21}=(k_y/k_0)(B_{reduced}^s)^{-1}(K_xE^{-1})_{reduced}^sW_1, \qquad \text{eq. 120}$$

$$V_{22}=(B_{reduced}^s)^{-1}W_2Q_2, \qquad \text{eq. 121}$$

where $Q_1$, $W_1$, $Q_2$, and $W_2$ are the eigenvalue and eigenvector matrices for the new, reduced eigen-problems of eqs. 85 and 107.

This new, reduced eigen-system, combined with the reduced boundary problem, gives exactly the same diffracted amplitudes and diffraction efficiencies as the old formulation for phi=90 for any given truncation order, N, but with much improved computational efficiency. For a given order, N, the computation speed is reduced by a factor of approximately 8 compared to the old formulation.

In some cases, the new, reduced phi=90 algorithms can be significantly faster than even the corresponding classical mount problem with the same polar incidence angle. In the theoretical best case limit, the phi=90 case requires about 62.5% the time as the corresponding classical case. This assumes that the eigen-problem and boundary value problem require equal amounts of time to solve for a given truncation order, N. In practice, this is more or less realized for lower truncation orders. Such a speed advantage can quickly add up when considering the amount of time that may be required to generate a library of several million spectra. In such cases, it may be beneficial to use the phi=90 mount only.

In the other limiting case where a very large truncation order is required, the computation time is basically dominated by the large matrix inversion in the boundary problem (eq. 47). In this limit, the phi=90 case requires approximately 92.5% of the computation time as the phi=0 case. Steps can be taken to make the matrix inversion more efficient, since only the top half is used, which is of some help.

These estimates ignore the fact that there is a little more overhead when constructing the various matrices for the phi=90 case than with the phi=0 case. In practice, the differences in computation speed ranges from being about equal for the phi=90 and phi=0 cases to a 20-30% speed improvement for the phi=90 mount over the corresponding phi=0 case. Either way, the improvement over the old phi=90 formulation is quite significant, and the ideas outlined in the introduction section involving multiple azimuthal datasets can be employed without a disabling increase in computation cost.

To complete the description, the reduced eigen-system is derived for p polarized incident light in the phi=90 conical mount. In this case, the fields satisfy $$R_{s,i} = -R_{s,-i} \qquad \text{eq. 122}$$

$$R_{p,i} = R_{p,-i} \qquad \text{eq. 123}$$

$$T_{s,i} = -T_{s,-i} \qquad \text{eq. 124}$$

$$T_{p,i} = T_{p,-i}, \qquad \text{eq. 125}$$

in regions I and II, and $$S_{x,i} = -S_{x,-i} \qquad \text{eq. 126}$$

$$S_{y,i} = S_{y,-i} \qquad \text{eq. 127}$$

$$U_{x,i} = U_{x,-i} \qquad \text{eq. 128}$$

$$U_{y,i} = -U_{y,-i}, \qquad \text{eq. 129}$$

in the grating region.

Eqs. 122-129 applied to the boundary problem lead to the same conclusion as in the s-polarized incidence case, except in this case add the i and −i terms for eqs. 28, 29, 35, and 36, and subtract the −ith from the ith terms in eqs. 26, 27, 33, and 34.

Again, the boundary matching at z=0 and z=d leads to eqs. 26-41 for the boundary equations, but with N+1 sized vectors $R_s$, $R_p$, $T_s$, and $T_p$, so long as it is again possible to reduce the eigen-problem as well.

To do this, start with eq. 16 and apply the case 1 reduction:

$$\frac{\partial^2 U_{x0}}{\partial (z')^2} = \frac{k_y^2}{k_0^2} U_{x0} - \left\{ E_{0,0} U_{x,0} + \sum_{m=1}^{\infty} \begin{pmatrix} E_{0,m} + \\ E_{0,-m} \end{pmatrix} U_{xm} \right\} \qquad \text{eq. 130}$$

$$\frac{\partial^2 U_{xi}}{\partial (z')^2} = \frac{k_y^2}{k_0^2} U_{xi} + \frac{k_{xi}^2}{k_0^2} U_{xi} - \left\{ \begin{array}{l} \frac{1}{2}(E_{i,0} + E_{-i,0}) U_{x0} + \\ \frac{1}{2} \sum_{m=1}^{\infty} \begin{pmatrix} E_{i,m} + \\ E_{-i,-m} + \\ E_{i,-m} \end{pmatrix} U_{xm} \end{array} \right\} \qquad \text{eq. 131}$$

which shows that $E_{reduced}$ is given by $$E_{i,0} U_{x0} + \sum_{m=1}^{\infty} (E_{0,m} + E_{0,-m}) U_{xm}, \, i = 0, \qquad \text{eq. 132}$$

and $$\frac{1}{2}(E_{i,0} + E_{-i,0}) U_{x0} + \frac{1}{2} \sum_{m=1}^{\infty} \begin{pmatrix} E_{i,m} + E_{-i,-m} + \\ E_{-i,m} + E_{i,-m} \end{pmatrix} U_{xm}, \, i > 0, \qquad \text{eq. 133}$$

or $$E^p_{reduced} = \qquad \text{eq. 134}$$

$$\begin{bmatrix} E_{0,0} & E_{0,1} + E_{0,-1} & E_{0,2} + E_{0,-2} & \cdots \\ \frac{1}{2}\begin{pmatrix} E_{1,0} + \\ E_{-1,0} \end{pmatrix} & \frac{1}{2}\begin{pmatrix} E_{1,1} + E_{-1,-1} + \\ E_{1,-1} + E_{-1,1} \end{pmatrix} & \frac{1}{2}\begin{pmatrix} E_{1,2} + E_{-1,-2} + \\ E_{1,-2} + E_{-1,2} \end{pmatrix} & \cdots \\ \frac{1}{2}\begin{pmatrix} E_{2,0} + \\ E_{-2,0} \end{pmatrix} & \frac{1}{2}\begin{pmatrix} E_{2,1} + E_{-2,-1} + \\ E_{2,-1} + E_{-2,1} \end{pmatrix} & \frac{1}{2}\begin{pmatrix} E_{2,2} + E_{-2,-2} + \\ E_{2,-2} + E_{-1,2} \end{pmatrix} & \cdots \\ \vdots & & & \ddots \end{bmatrix}$$

Using $$A_{reduced}^p = K_x^2 - E_{reduced}^p, \qquad \text{eq. 135}$$

eq. 16 becomes $$[\partial^2 U_x/\partial (z')^2] = [K_y^2 + A_{reduced}^p][U_x] \qquad \text{eq. 136}$$

where the indices on $U_x$ run from 0 to N, and $K_x$ and $K_y$ are reduced as in the s polarization case.

For eq. 17, case 2 could be applied directly to the product $BEinv^{-1}$, but a more efficient set of operations is to proceed as in the s polarization case. $Einv^{-1}$ is reduced by applying case 2 to eq. 103:

$$\frac{\partial U_{y0}}{\partial z'} = \ldots + (Einv^{-1})_{0,0} S_{x0}, \, i = 0, \qquad \text{eq. 137}$$

$$\frac{\partial U_{yi}}{\partial z'} = \ldots + \sum_{m=1}^{\infty} [(Einv^{-1})_{i,m} - (Einv^{-1})_{i,-m}] S_{xm}, \, i > 0, \qquad \text{eq. 138}$$

or $$(Einv^{-1})_{reduced}^p = \begin{bmatrix} (Einv^{-1})_{0,0} & 0 & 0 & \cdots \\ 0 & (Einv^{-1})_{1,1} - (Einv^{-1})_{1,2} - \\ & (Einv^{-1})_{1,-1} & (Einv^{-1})_{1,-2} & \cdots \\ 0 & (Einv^{-1})_{2,1} - (Einv^{-1})_{2,2} - \\ & (Einv^{-1})_{2,-1} & (Einv^{-1})_{2,-2} & \cdots \\ \vdots & & & \ddots \end{bmatrix} \qquad \text{eq. 139}$$

where the fact that $(Einv^{-1})_{i,m} = (Einv^{-1})_{-i,-m}$ is utilized.

For B, explicitly reduce the product $K_x E^{-1} K_x$:

$$\frac{\partial S_{xi}}{\partial (z')} = \ldots + \frac{k_{xi}}{k_0} \sum_{m=-\infty}^{\infty} (E^{-1})_{i,m} \frac{k_{xm}}{k_0} U_{ym}. \qquad \text{eq. 140}$$

Subtracting the −i th row from the i th row:

$$\frac{\partial S_{x0}}{\partial (z')} = \ldots + 0, \, i = 0, \qquad \text{eq. 141}$$

since $k_{x0} = 0$, and $$2\frac{\partial S_{xi}}{\partial (z')} = \ldots + \frac{k_{xi}}{k_0} \sum_{m=-\infty}^{\infty} (E^{-1})_{i,m} \frac{k_{xm}}{k_0} U_{ym} - \frac{k_{x-i}}{k_0} \sum_{m=-\infty}^{\infty} (E^{-1})_{i,m} \frac{k_{xm}}{k_0} U_{ym}$$

$$= \ldots + \frac{k_{xi}}{k_0}\left[\begin{array}{l}\sum_{m=-\infty}^{-1}(E^{-1})_{i,m}\frac{k_{xm}}{k_0}U_{ym}+\\\sum_{m=-\infty}^{\infty}(E^{-1})_{i,m}\frac{k_{xm}}{k_0}U_{ym}\end{array}\right]-$$

$$\frac{k_{x-i}}{k_0}\left[\begin{array}{l}\sum_{m=-\infty}^{-1}(E^{-1})_{-i,m}\frac{k_{xm}}{k_0}U_{ym}+\\\sum_{m=1}^{\infty}(E^{-1})_{-i,m}\frac{k_{xm}}{k_0}U_{ym}\end{array}\right]$$

$$= \ldots + \frac{k_{xi}}{k_0}\left[\begin{array}{l}-\sum_{m=1}^{\infty}(E^{-1})_{i,-m}\frac{k_{x-m}}{k_0}U_{ym}+\\\sum_{m=1}^{\infty}(E^{-1})_{i,m}\frac{k_{xm}}{k_0}U_{ym}\end{array}\right]-$$

$$\frac{k_{x-i}}{k_0}\left[\begin{array}{l}-\sum_{m=1}^{\infty}(E^{-1})_{-i,-m}\frac{k_{x-m}}{k_0}U_{ym}+\\\sum_{m=1}^{\infty}(E^{-1})_{-i,m}\frac{k_{xm}}{k_0}U_{ym}\end{array}\right]$$

$$= \ldots + \frac{k_{x-i}}{k_0}\left[\begin{array}{l}\sum_{m=1}^{\infty}(E^{-1})_{i,-m}\frac{k_{x-m}}{k_0}U_{ym}+\\\sum_{m=1}^{\infty}(E^{-1})_{i,m}\frac{k_{xm}}{k_0}U_{ym}\end{array}\right]-$$

$$\frac{k_{x-i}}{k_0}\left[\begin{array}{l}\sum_{m=1}^{\infty}(E^{-1})_{-i,-m}\frac{k_{x-m}}{k_0}U_{ym}+\\\sum_{m=1}^{\infty}(E^{-1})_{-i,m}\frac{k_{xm}}{k_0}U_{ym}\end{array}\right]$$

$$= \ldots + \frac{k_{xi}}{k_0}\left[\begin{array}{l}\sum_{m=1}^{\infty}(E^{-1})_{i,-m}\frac{k_{xm}}{k_0}U_{ym}+\\\sum_{m=1}^{\infty}(E^{-1})_{i,m}\frac{k_{xm}}{k_0}U_{ym}\end{array}\right]+$$

$$\frac{k_{x-i}}{k_0}\left[\begin{array}{l}\sum_{m=1}^{\infty}(E^{-1})_{-i,-m}\frac{k_{xm}}{k_0}U_{ym}+\\\sum_{m=1}^{\infty}(E^{-1})_{-i,m}\frac{k_{xm}}{k_0}U_{ym}\end{array}\right]$$

$$= \ldots + \frac{k_{xi}}{k_0}\left[\begin{array}{l}\sum_{m=1}^{\infty}(E^{-1})_{i,-m}\frac{k_{xm}}{k_0}U_{ym}+\\\sum_{m=1}^{\infty}(E^{-1})_{i,m}\frac{k_{xm}}{k_0}U_{ym}+\\\sum_{m=1}^{\infty}(E^{-1})_{-i,-m}\frac{k_{xm}}{k_0}U_{ym}+\\\sum_{m=1}^{\infty}(E^{-1})_{-i,m}\frac{k_{xm}}{k_0}U_{ym}\end{array}\right]$$

$$= \ldots + \frac{k_{xi}}{k_0}\sum_{m=1}^{\infty}\left[\begin{array}{l}(E^{-1})_{i,-m}+(E^{-1})_{i,m}+\\(E^{-1})_{-i,-m}+(E^{-1})_{-i,m}\end{array}\right]\frac{k_{xm}}{k_0}u_{ym}$$

$$= \ldots + \frac{k_{xi}}{k_0}\sum_{m=1}^{\infty}[2(E^{-1})_{i,m}+2(E^{-1})_{i,-m}]\frac{k_{xm}}{k_0}u_{ym}$$

giving $$\frac{\partial S_{xi}}{\partial(z')} = \ldots + \frac{k_{xi}}{k_0}\sum_{m=1}^{\infty}[(E^{-1})_{i,m}+(E^{-1})_{i,-m}]\frac{k_{xm}}{k_0}U_{ym}, i>0, \quad \text{eq. 142}$$

which implies $$(K_xE^{-1}K_x)^p_{reduced} = \quad \text{eq. 143}$$

$$\begin{bmatrix} 0 & 0 & 0 & \cdots \\ 0 & \frac{k_{x1}}{k_0}\left[\begin{array}{l}(E^{-1})_{1,1}+\\(E^{-1})_{1,-1}\end{array}\right]\frac{k_{x1}}{k_0} & \frac{k_{x1}}{k_0}\left[\begin{array}{l}(E^{-1})_{1,2}+\\(E^{-1})_{1,-2}\end{array}\right]\frac{k_{x2}}{k_0} & \cdots \\ 0 & \frac{k_{x2}}{k_0}\left[\begin{array}{l}(E^{-1})_{2,1}+\\(E^{-1})_{2,-1}\end{array}\right]\frac{k_{x1}}{k_0} & \frac{k_{x2}}{k_0}\left[\begin{array}{l}(E^{-1})_{2,2}+\\(E^{-1})_{2,-2}\end{array}\right]\frac{k_{x2}}{k_0} & \cdots \\ \cdots & & & \ddots \end{bmatrix}$$

in explicit form. Then $$B_{reduced}{}^p = (K_xE^{-1}K_x)_{reduced}{}^p - I \quad \text{eq. 144}$$

and eq. 17 becomes $$[\partial^2 S_x/\partial(z')^2] = [K_y^2 + B_{reduced}{}^p(Einv^{-1})_{reduced}{}^p][S_x], \quad \text{eq. 145}$$

where again the indices run from 0 to N and $K_y$ is reduced as in the s polarization case.

The corresponding equations to replace eqs 21-25 are found in a similar manner as before. Most of the verification steps are omitted here. $A^{-1}$ and $B^{-1}$ are replaced by $(A_{reduced})^{-1}$ and $(B_{reduced})^{-1}$ as before. To find $K_xE^{-1}$ in eq. 24, use eq. 111 with case 4:

$$\frac{\partial S_{x0}}{\partial(z')} = \ldots - \left\{\begin{array}{l}(K_xE^{-1})_{0,0}U_{x0}+\\\sum_{m=1}^{\infty}\left[\begin{array}{l}(K_xE^{-1})_{0,m}+\\(K_xE^{-1})_{0,-m}\end{array}\right]U_{xm}\end{array}\right\} i=0, \quad \text{eq. 146}$$

and $$\frac{\partial S_{xi}}{\partial(z')} = -\left\{\begin{array}{l}\frac{1}{2}\left[\begin{array}{l}(K_xE^{-1})_{i,0}-\\(K_xE^{-1})_{-i,0}\end{array}\right]U_{x0}+\\\frac{1}{2}\sum_{m=1}^{\infty}\left[\begin{array}{l}(K_xE^{-1})_{i,m}+\\(K_xE^{-1})_{i,-m}-\\(K_xE^{-1})_{-i,-m}-\\(K_xE^{-1})_{-i,-m}\end{array}\right]U_{xm}\end{array}\right\}, i>0. \quad \text{eq. 147}$$

This gives $$(K_xE^{-1})^p_{reduced} = \quad \text{eq. 148}$$

$$\begin{bmatrix} (K_xE^{-1})_{0,0} & (K_xE^{-1})_{0,1}+(K_xE^{-1})_{0,-1} & \cdots \\ \frac{1}{2}\left[\begin{array}{l}(K_xE^{-1})_{1,0}-\\(K_xE^{-1})_{-1,0}\end{array}\right] & \frac{1}{2}\left[\begin{array}{l}(K_xE^{-1})_{1,1}+(K_xE^{-1})_{1,-1}-\\(K_xE^{-1})_{-1,1}-(K_xE^{-1})_{-1,-1}\end{array}\right] & \cdots \\ \frac{1}{2}\left[\begin{array}{l}(K_xE^{-1})_{2,0}-\\(K_xE^{-1})_{-2,0}\end{array}\right] & \frac{1}{2}\left[\begin{array}{l}(K_xE^{-1})_{2,1}+(K_xE^{-1})_{2,-1}-\\(K_xE^{-1})_{-2,1}-(K_xE^{-1})_{-2,-1}\end{array}\right] & \cdots \\ \vdots & & \ddots \end{bmatrix}$$

Putting all of this together, eqs. 22-25 for p polarized incidence are replaced by $$V_{11} = (A_{reduced}^p)^{-1} W_1 Q_1, \quad \text{eq. 149}$$

$$V_{12} = (k_y/k_0)(A_{reduced}^p)^{-1} K_x W_2, \quad \text{eq. 150}$$

$$V_{21} = (k_y/k_0)(B_{reduced}^p)^{-1} (K_x E^{-1})_{reduced}^p W_1, \quad \text{eq. 151}$$

$$V_{22} = (B_{reduced}^p)^{-1} W_2 Q_2, \quad \text{eq. 152}$$

where $Q_1$, $W_1$, $Q_2$, and $W_2$ are the eigenvalue and eigenvector matrices for the new, reduced eigen-problems of eqs. 136 and 145. The speed improvement is very similar to the s polarization case.

After solving the reduced boundary problem for the particular s or p incidence case, the diffraction efficiencies can be obtained from $$DE_{ri} = |R_{s,i}|^2 \text{Re}\left(\frac{k_{I,zi}}{k_0 n_I \cos\theta}\right) + |R_{p,i}|^2 \text{Re}\left(\frac{k_{I,zi}/n_I^2}{k_0 n_I \cos\theta}\right). \quad \text{eq. 153}$$

For i=0, eq. 153 is just the specular reflectance for the given incident condition.

It should be pointed out that the only assumption about the grating permittivity expansion coefficients was the symmetry exploited in Eq. 76. In other words, the specific form of the permittivity Fourier coefficients for a binary grating shown in Eq. 9 were not explicitly used in the above descriptions. The grating can consist of more than 2 different materials with differing optical properties, the only difference being that the permittivity Fourier coefficients are different from the coefficients given for the binary structure in Eq. 9. The grating should still satisfy Eq. 76 where required. Additionally, as with the conventional formulation, profile shapes other than rectangular can be treated using a staircase approximation consisting of multiple rectangular grating layers.

The calculated diffraction efficiencies or amplitudes can be used to compute polarized or unpolarized reflectance data, ellipsometric data, or polarimetric data. During an optical grating measurement, one or more datasets are generated by varying the incident wavelength, polar angle of incidence, theta, and rotating the azimuthal angle of incidence between 0 degrees and 90 degrees. The optical data of the one or more datasets are compared to data generated from a theoretical model of the grating using the above calculation methods. A regression analysis is used to optimize the parameters of the theoretical grating model. The result of the optical measurement is given by the optimized grating parameters. The average of the s and p incident calculations can be used to analyze unpolarized reflectance.

The regression algorithm can be the Simplex or Levenberg-Marquardt algorithms, described in W. H. Press, S. A. Teukolsky, W. T. Vetterling, and B. P. Flannery, *Numerical Recipes in C* ($2^{nd}$ Edition), Cambridge University Press, Cambridge, 1992, among others, or can even consist of a simple parameter grid search. The model calculation can be performed in real-time (at the time of measurement), using one or multiple CPUs. The theoretical model spectra can also be pre-calculated ahead of time, generating a library database of spectra, from which the calculation result can be rapidly extracted during the measurement. A neural network can be pre-generated, from which the best-fit model can be directly extracted using a fixed number of relatively simple calculation steps during the measurement.

In many cases, specularly reflected, transmitted, and/or diffracted intensities are detected, and the optical system can be calibrated to give reflectance (0 R diffraction efficiency), transmittance, or diffraction efficiency. However, in some cases, particularly for VUV reflectance work, it may be beneficial to normalize some of the intensities with intensities from other structures or from different incidence conditions. These ratios are independent of incident intensity, and a system calibration that involves determining incident intensity may be skipped. The analysis can be done by calculating the corresponding reflectance or diffraction efficiency ratios. For example, a first dataset may be reflected (0 order) intensity I(0) due to unpolarized light incident at phi=0, and the second dataset may be reflected (0 order) intensity I(90) due to unpolarized light incident at phi=90. The incident intensity will typically not change over short time periods, so if the datasets are collected in close succession, the intensity ratio is the same as the reflectance ratio:

$$\frac{I(0)}{I(90)} = \frac{R(0)}{R(90)} \quad \text{eq. 154}$$

R(0) and R(90) can be calculated using the conventional phi=0 calculation and new phi=90 calculation presented above. A regression procedure might use the following merit function:

$$\chi^2 = \sum_{i=1}^{N} \left(\frac{1}{\sigma_i}\right)^2 \left(\left(\frac{R(0)}{R(90)}\right)_{i,measured} - \left(\frac{R(0)}{R(90)}\right)_{i,calculated}\right)^2 \quad \text{eq. 155}$$

where the subscript i refers to incident condition (usually wavelength), $\sigma_i$ is the estimated uncertainty of the measured reflectance ratio, and N is the total number of data points included for the ratio. The merit function is minimized by the regression procedure, thereby optimizing the grating parameters, which affect the calculated values for both numerator and denominator of the ratio. Note that in this case, the grating parameters are the same for both numerator and denominator.

As describe above the analysis of a diffraction grating problem is of particular use to determining the various characteristics of the diffraction grating structure including, for example, the critical dimensions and the composition of a diffraction grating. The analysis techniques described herein are of particular use in reducing the complexity and increase the speed of such analysis, which is of particular importance in high volume manufacturing processes. It will be recognized that the diffraction problem analysis techniques described herein may be utilized in a wide range of applications where is desirable to analysis a diffraction grating to obtain any of a wide range of types of characteristics of the grating structure.

Further modifications and alternative embodiments of this invention will be apparent to those skilled in the art in view of this description. It will be recognized, therefore, that the present invention is not limited by these example arrangements. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the implementations and architectures. For example, equivalent elements may be substituted for those illustrated and described herein, and certain features of the invention may be utilized independently of the use of other features, all as would be apparent to one skilled in the art after having the benefit of this description of the invention.

What is claimed is:

1. A method of characterizing a diffraction grating structure, comprising
collecting a first set of reflected data from the grating structure by providing incident light at a first angle of azimuthal incidence with respect to the grating structure;
collecting a second set of reflected data from the grating structure by providing incident light at a second angle of azimuthal incidence with respect to the grating structure, the first and second angles being effectively orthogonal and the second angle of azimuthal incidence being different from zero;
analyzing a combination of at least the first and second set of reflected data; and
utilizing symmetrical characteristics of a diffraction analysis of the second angle of azimuthal incidence reflected data so as to reduce the computation complexity of the analysis of the second set of reflected data during the determination of at least one geometrical characteristic of the grating structure,
where one or more of the sets of data are used to normalize other set(s) of data so that optical metrology data comprises ratios of reflected data collected for different incident conditions, avoiding the need to determine incident intensity via an absolute calibration process.

2. The method of claim 1, wherein the optical metrology data comprises a first ratio of at least a portion of the first set of reflected data and at least a portion of the second set of reflected data.

3. The method of claim 2, wherein the diffraction analysis comprises a regression or library lookup procedure that minimizes the difference between a calculated reflectance or diffraction efficiency ratio and a measured intensity ratio.

4. The method of claim 3, wherein an inverse ratio is substituted in specific wavelength regions where the denominator of the first ratio is near zero.

5. The method of claim 4, wherein a weighting function is used to equalize a contribution to a merit function regardless of a reflectance ratio magnitude.

6. The method of claim 3, wherein data regions at which a denominator of the first ratio is near zero are dropped from the diffraction analysis.

7. The method of claim 1, where one or more diffracted orders of reflected data are detected along with or instead of the 0'th order.

8. The method of claim 1, wherein data is only collected at the first azimuthal angle and the second azimuthal angle.

9. The method of claim 8, wherein the diffraction analysis comprises utilizing a rigorous coupled wave analysis.

10. The method of claim 1, wherein four data sets are utilized in the diffraction analysis for each polar angle, the data sets being comprised of two different polarizations at each of the first and second azimuthal angles.

11. The method of claim 1, further comprising utilizing multiple polar angles at each of the first and second azimuthal angles.

12. The method of claim 1, wherein the diffraction analysis comprises utilizing a rigorous coupled wave analysis.

13. The method of claim 12, wherein the symmetry properties comprise symmetry properties of the Fourier expansions of the rigorous coupled wave (RCW) analysis for the second azimuthal angle, allowing RCW eigen- and boundary problems to be reduced in complexity.

14. The method of claim 13, wherein a second azimuthal angle boundary problem is reduced to a $4(N+1) \times 4(N+1)$ system of equations and an eigen-problem is reduced to two $(N+1) \times (N+1)$ eigen-systems for a given truncation order, N.

15. The method of claim 14, where each of the various matrices of the eigenproblems are reduced according to one of
1) $\epsilon_{0,0}$ for i=m=0, $(\epsilon_{0,m}+\epsilon_{0,-m})$ for i=0 and m>0, $\frac{1}{2}(\epsilon_{i,0}+\epsilon_{-i,0})$ for i>0 and m=0, and $\frac{1}{2}(\epsilon_{i,m}+\epsilon_{-i,-m}+\epsilon_{i,-m}+\epsilon_{-i,m})$ for i,m>0,
2) $\epsilon_{0,0}$ for i=m=0, $(\epsilon_{0,m}-\epsilon_{0,-m})$ for i=0 and m>0, $\frac{1}{2}(\epsilon_{i,0}-\epsilon_{-i,0})$ for i>0 and m=0, and $\frac{1}{2}(\epsilon_{i,m}+\epsilon_{-i,-m}-\epsilon_{-i,m}-\epsilon_{i,-m})$ for i,m>0,
3) $\epsilon_{0,0}$ for i=m=0, $(\epsilon_{0,m}-\epsilon_{0,-m})$ for i=0 and m>0, $\frac{1}{2}(\epsilon_{i,0}+\epsilon_{-i,0})$ for i>0 and m=0, and $\frac{1}{2}(\epsilon_{i,m}+\epsilon_{-i,m}-\epsilon_{i,-m}-\epsilon_{-i,-m})$ for i,m>0, or
4) $\epsilon_{0,0}$ for i=m=0, $(\epsilon_{0,m}+\epsilon_{0,-m})$ for i=0 and m>0, $\frac{1}{2}(\epsilon_{i,0}-\epsilon_{-i,0})$ for i>0 and m=0, and $\frac{1}{2}(\epsilon_{i,m}+\epsilon_{i,-m}-\epsilon_{-i,m}-\epsilon_{-i,-m})$ for i,m>0,
depending on the symmetry conditions obeyed by the original, unreduced coupled equations, and where $\epsilon_{i,m}$, $-N \leq i, m \leq N$, are the elements of the unreduced matrices.

16. The method of claim 14, where one of the eigenproblem matrices is reduced according to $\epsilon_{0,0}$ for i=m=0, $(\epsilon_{0,m}+\epsilon_{0,-m})$ for i=0 and m>0, $\frac{1}{2}(\epsilon_{i,0}+\epsilon_{-i,0})$ for i>0 and m=0, and $\frac{1}{2}(\epsilon_{i,m}+\epsilon_{-i,-m}+\epsilon_{i,-m}+\epsilon_{-i,m})$ for i,m>0, and the second matrix is reduced according to $\gamma_{0,0}$ for i=m=0, $(\gamma_{0,m}-\gamma_{0,-m})$ for i=0 and m>0, $\frac{1}{2}(\gamma_{i,0}-\gamma_{-i,0})$ for i>0 and m=0, and $\frac{1}{2}(\gamma_{i,m}+\gamma_{-i,-m}-\gamma_{-i,m}-\gamma_{i,-m})$ for i,m>0, where $\epsilon_{i,m}$ and $\gamma_{i,m}$, $-N \leq i,m \leq N$, are the elements of the unreduced matrices.

17. The method of claim 16, where the first matrix is BE and the second matrix is E for s incident polarization, and vice versa for p incident polarization, resulting in reduced eigenproblems $K_y^2+(BE)_{reduced}$ and $K_y^2+K_x^2-E_{reduced}$, where $K_y^2$ and $K_x^2$ are diagonal matrices with elements consisting of the 0, ..., N elements of the unreduced diagonal matrices.

18. The method of claim 16, where the first matrix is $BEinv^{-1}$ and the second matrix is E for s incident polarization, and vice versa for p incident polarization, resulting in reduced eigenproblems $K_y^2+(BEinv^{-1})_{reduced}$ and $K_y^2+K_x^2-E_{reduced}$, where $K_y^2$ and $K_x^2$ are diagonal matrices with elements consisting of the 0, ..., N elements of the unreduced diagonal matrices.

* * * * *